US010912771B1

(12) United States Patent
O'Brien et al.

(10) Patent No.: US 10,912,771 B1
(45) Date of Patent: Feb. 9, 2021

(54) METHODS FOR THE ADMINISTRATION OF CERTAIN VMAT2 INHIBITORS

(71) Applicant: Neurocrine Biosciences, Inc., San Diego, CA (US)

(72) Inventors: Christopher F. O'Brien, San Diego, CA (US); Haig P. Bozigian, San Diego, CA (US)

(73) Assignee: Neurocrine Biosciences, Inc., San Diego, CA (US)

(*) Notice: Subject to any disclaimer, the term of this patent is extended or adjusted under 35 U.S.C. 154(b) by 0 days.

(21) Appl. No.: 17/073,304

(22) Filed: Oct. 17, 2020

Related U.S. Application Data

(63) Continuation of application No. 16/481,033, filed as application No. PCT/US2017/055877 on Oct. 10, 2017.

(60) Provisional application No. 62/451,605, filed on Jan. 27, 2017.

(51) Int. Cl.
*A61K 31/4745* (2006.01)

(52) U.S. Cl.
CPC .................. *A61K 31/4745* (2013.01)

(58) Field of Classification Search
CPC .... A61K 31/4375; A61K 9/0053; A61K 9/48; A61K 31/4525; A61K 31/4745; A61P 25/14; C07D 455/06
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,328,245 A | 5/1982 | Yu et al. |
| 4,409,239 A | 10/1983 | Yu |
| 4,410,545 A | 10/1983 | Yu et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,612,059 A | 3/1997 | Cardinal et al. |
| 5,639,476 A | 6/1997 | Oshlack et al. |
| 5,639,480 A | 6/1997 | Bodmer et al. |
| 5,674,533 A | 10/1997 | Santus et al. |
| 5,698,220 A | 12/1997 | Cardinal et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gorewich |
| 5,798,119 A | 8/1998 | Herbig et al. |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Heynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,350,458 B1 | 2/2002 | Modi |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |

(Continued)

FOREIGN PATENT DOCUMENTS

| | | |
|---|---|---|
| EP | 1716145 | 11/2006 |
| JP | 57-077697 | 5/1982 |

(Continued)

OTHER PUBLICATIONS

U.S. Appl. No. 16/481,033, O'Brien et al., filed Jul. 25, 2019.
U.S. Appl. No. 16/481,034, O'Brien et al., filed Jul. 25, 2019.
U.S. Appl. No. 16/481,037, O'Brien et al., filed Jul. 25, 2019.
U.S. Appl. No. 16/509,552, McGee et al., filed Jul. 12, 2019.
U.S. Appl. No. 16/608,521, O'Brien, filed Oct. 25, 2019.
U.S. Appl. No. 16/646,866, Moore Jr. et al., filed Mar. 12, 2020.
U.S. Appl. No. 16/651,887, O'Brien et al., filed Mar. 27, 2020.
U.S. Appl. No. 16/662,346, McGee et al., filed Oct. 24, 2019.
U.S. Appl. No. 16/701,339, O'Brien et al., filed Dec. 3, 2019.

(Continued)

*Primary Examiner* — Amanda L. Aguirre

(74) *Attorney, Agent, or Firm* — Fish & Richardson P.C.

(57) ABSTRACT

Provided are methods of administering a vesicular monoamine transport 2 (VMAT2) inhibitor chosen from valbenazine and (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof to a patient in need thereof wherein the patient is being treated with a strong cytochrome P450 3A4 (CYP3A4) inducer.

15 Claims, No Drawings

(56) References Cited

U.S. PATENT DOCUMENTS

| | | |
|---|---|---|
| 6,699,500 B2 | 3/2004 | Okada et al. |
| 8,039,627 B2 | 10/2011 | Gano et al. |
| 8,357,697 B2 | 1/2013 | Gano et al. |
| 8,524,733 B2 | 9/2013 | Gant et al. |
| 9,714,246 B2 | 7/2017 | Ashweek et al. |
| 9,782,398 B2 | 10/2017 | Hoare et al. |
| 10,065,952 B2 | 9/2018 | McGee et al. |
| 10,160,757 B2 | 12/2018 | McGee et al. |
| 10,689,380 B1 | 6/2020 | Lopez |
| 2006/0051345 A1 | 3/2006 | Frohna |
| 2006/0241082 A1 | 10/2006 | Fleckenstein et al. |
| 2008/0108645 A1 | 5/2008 | Tridgett et al. |
| 2008/0167337 A1 | 7/2008 | Gano |
| 2009/0209755 A1 | 8/2009 | Suzuki et al. |
| 2010/0076087 A1 | 3/2010 | Gant et al. |
| 2011/0053866 A1 | 3/2011 | Duffield et al. |
| 2012/0003330 A1 | 1/2012 | Gant et al. |
| 2012/0077839 A1 | 3/2012 | Gano |
| 2014/0187505 A1 | 7/2014 | Pollard |
| 2014/0341994 A1 | 11/2014 | Sommer et al. |
| 2015/0004231 A1 | 1/2015 | Sommer et al. |
| 2015/0025086 A1 | 1/2015 | Dressman et al. |
| 2016/0030414 A1 | 2/2016 | Gant et al. |
| 2016/0339011 A1 | 11/2016 | Hoare et al. |
| 2016/0346200 A1 | 12/2016 | Sommer et al. |
| 2016/0346270 A1 | 12/2016 | Stamler |
| 2017/0071932 A1 | 3/2017 | O'Brien |
| 2017/0145008 A1 | 5/2017 | McGee et al. |
| 2017/0183346 A1 | 6/2017 | McGee et al. |
| 2018/0085364 A1 | 3/2018 | Hoare |
| 2018/0333409 A1* | 11/2018 | Srinivasan ......... A61K 31/4985 |
| 2019/0015396 A1 | 1/2019 | O'Brien |
| 2019/0262328 A1* | 8/2019 | Srinivasan ......... A61K 31/4745 |
| 2019/0381016 A1 | 12/2019 | O'Brien et al. |
| 2019/0381029 A1 | 12/2019 | Hoare et al. |
| 2020/0078352 A1 | 3/2020 | O'Brien |
| 2020/0093808 A1 | 3/2020 | O'Brien et al. |
| 2020/0101063 A1 | 4/2020 | O'Brien et al. |
| 2020/0179352 A1 | 6/2020 | O'Brien |
| 2020/0181140 A1 | 6/2020 | McGee et al. |
| 2020/0206215 A1 | 7/2020 | Hoare et al. |
| 2020/0230127 A1 | 7/2020 | O'Brien et al. |
| 2020/0268724 A1 | 8/2020 | O'Brien et al. |
| 2020/0268725 A1 | 8/2020 | O'Brien et al. |
| 2020/0268743 A1 | 8/2020 | O'Brien et al. |
| 2020/0268744 A1 | 8/2020 | O'Brien et al. |
| 2020/0268745 A1 | 8/2020 | O'Brien et al. |
| 2020/0276184 A1 | 9/2020 | Moore, Jr. et al. |

FOREIGN PATENT DOCUMENTS

| | | | |
|---|---|---|---|
| JP | 57-209225 | 12/1982 | |
| WO | WO 1991/019498 | 12/1991 | |
| WO | WO 1998/011897 | 3/1998 | |
| WO | WO 2000/024399 | 5/2000 | |
| WO | WO 2002/017918 | 3/2002 | |
| WO | WO 2005/077946 | 8/2005 | |
| WO | WO 2007/017654 | 2/2007 | |
| WO | WO 2008/058261 | 5/2008 | |
| WO | WO 2009/056885 | 5/2009 | |
| WO | WO-2010018408 A2 * | 2/2010 | ........... A61K 9/2054 |
| WO | WO 2010/026435 | 3/2010 | |
| WO | WO 2010/026436 | 3/2010 | |
| WO | WO 2010/044961 | 4/2010 | |
| WO | WO 2010/044981 | 4/2010 | |
| WO | WO 2011/019956 | 2/2011 | |
| WO | WO 2011/153157 | 12/2011 | |
| WO | WO 2014/047167 | 3/2014 | |
| WO | WO 2014/120654 | 8/2014 | |
| WO | WO 2015/077521 | 5/2015 | |
| WO | WO 2015/112707 | 7/2015 | |
| WO | WO 2015/120110 | 8/2015 | |
| WO | WO 2015/120317 | 8/2015 | |
| WO | WO 2015/171802 | 11/2015 | |
| WO | WO 2016/127133 | 8/2016 | |
| WO | WO 2016/144901 | 9/2016 | |
| WO | WO 2016/210180 | 12/2016 | |
| WO | WO 2017/075340 | 5/2017 | |
| WO | WO 2017/112857 | 6/2017 | |
| WO | WO 2018/102673 | 6/2018 | |
| WO | WO 2018/140092 | 8/2018 | |
| WO | WO 2018/140093 | 8/2018 | |
| WO | WO 2018/140094 | 8/2018 | |
| WO | WO 2018/140095 | 8/2018 | |
| WO | WO 2018/140096 | 8/2018 | |
| WO | WO 2018/200605 | 11/2018 | |
| WO | WO 2019/060322 | 3/2019 | |
| WO | WO 2019/074492 | 4/2019 | |
| WO | WO 2019/241555 | 12/2019 | |
| WO | WO 2020/037022 | 2/2020 | |

OTHER PUBLICATIONS

U.S. Appl. No. 16/754,658, O'Brien et al., filed Apr. 8, 2020.
U.S. Appl. No. 16/817,723, Hoare et al., filed Mar. 13, 2020.
U.S. Appl. No. 16/845,134, O'Brien et al., filed Apr. 10, 2020.
U.S. Appl. No. 16/870,423, O'Brien et al., filed May 8, 2020.
U.S. Appl. No. 16/870,572, O'Brien et al., filed May 8, 2020.
U.S. Appl. No. 16/870,706, O'Brien et al., filed May 8, 2020.
U.S. Appl. No. 16/870,823, O'Brien et al., filed May 8, 2020.
U.S. Appl. No. 16/871,528, O'Brien et al., filed May 11, 2020.
U.S. Appl. No. 16/899,641, McGee et al., filed Jun. 12, 2020.
U.S. Appl. No. 16/899,645, McGee et al., filed Jun. 12, 2020.
U.S. Appl. No. 16/899,654, McGee et al., filed Jun. 12, 2020.
U.S. Appl. No. 16/929,694, McGee et al., filed Jul. 15, 2020.
U.S. Appl. No. 16/929,696, McGee et al., filed Jul. 15, 2020.
U.S. Appl. No. 16/929,714, McGee et al., filed Jul. 15, 2020.
U.S. Appl. No. 16/929,716, McGee et al., filed Jul. 15, 2020.
U.S. Appl. No. 16/983,334, Liang et al., filed Aug. 3, 2020.
U.S. Appl. No. 16/989,206, Loewen et al., filed Aug. 10, 2020.
U.S. Appl. No. 17/005,425, O'Brien, filed Aug. 28, 2020.
U.S. Appl. No. 17/021,362, O'Brien et al., filed Sep. 15, 2020.
"Cytochrome P450 Oxidoreductase (POR) Deficiency," GeneDx, 2016, 5 pages.
"Neurocrine Valbenazine," Science IP Order 3198386, Oct. 2, 2019, 92 pages.
[No Author Listed], "Cytochrome P450 3A4 and 3A5 known drug interaction chart," 2014, 2 pages.
[No Author Listed], "Drug interactions with CYP3A inducers and inhibitors for Torisel (temsirolimus) injection," Wyeth Pharmaceuticals, 2008, 12 pages.
[No Author Listed], "Physician guidelines: drugs metabolized by cytochrome P450's," Genelex Corporation, 2005, 4 pages.
[No Author Listed]," Ingrezza Prescription Information," Neurocrine Biosciences, Apr. 2017, 16 pages.
Alexander et al., "Increased aggression in males in transgenic Tg2576 mouse model of Alzheimer's disease," Behav Brain Res., 216(1):77-83 (2011).
Anonymous, "11th Annual Meeting Schedule," ASENT, Mar. 5-7, 2009, 3 pages.
Anonymous, "12th Annual Meeting Program," ASENT, Bethesda, Maryland, Mar. 4-6, 2010, 1 page.
Anonymous, "Neurocrine Announces Phase IIb Results of VMAT2 Inhibitor NBI-98854 for Treatment of Tardive Dyskinesia," Neurocrine Biosciences: Investors: PressRelease, Sep. 9, 2013, [retrieved on Dec. 13, 2018] retrieved from URL<http://phoenix.corporate-ir.net/phoenix.zhtml?c=68817&p=irol-newsArticle_Print&Id=1853185>, 7 pages.
Australian Office Action in AU Appln. No. 2015256012, dated May 26, 2020, 5 pages.
Ballard et al., "Management of Agitation and Aggression Associated with Alzheimer's disease: controversies and possible solutions," Curr Opin in Psych., Nov. 2009, 22(6):532-540.
Ballard et al., "Neuroleptic drugs in dementia: benefits and harm," Nat Rev Neurosci., Jun. 2006, 7:492-500.
Ballard et al., "Quetiapine and rivastigmine and cognitive decline in Alzheimer's disease: randomised double blind placebo controlled trial," BMJ, Apr. 16, 2005, 330:874-877.

(56) References Cited

OTHER PUBLICATIONS

Bastin et al., "Salt Selection and Optimisation Procedures for Pharmaceutical New Chemical Entities," Organic Process Res. Dev., 2000, 4(5):427-435.
Bauer, "Pharmaceutical Solids—The Amorphous Phase," J Validation Tech., 2009, 15(3):63-68.
Berge et al., "Pharmaceutical Salts," J Pharm Sci., Jan. 1977, 66(1):1-19.
Bhidayasiri and Boonyawairoj, "Spectrum of tardive syndromes: clinical recognition and management.," Postgrad Med J, Feb. 2011, 87(1024): 132-141.
Boldt et al., "Synthesis of (+)- and (-)-Tetrabenazine from the Resolution of [alpha]-Dihydrotetrabenazine," Synthetic Communications, 2009, 39(20):3574-3585.
Brunner et al., "Comprehensive Analysis of the 16p11.2 Deletion and Null Cntnap2 Mouse Models of Autism Spectrum Disorder," PLoS One, Aug. 14, 2015, 10(8):e0134572.
Brusa et al., "Tetrabenazine improves levodopa-induced peak-dose dyskinesias in patients with Parkinson's disease," Funct. Neural., 2013, 28(2):101-5.
Bystritsky, " Treatment-resistant anxiety disorders," Mol. Psychiatry, Sep. 2006, 11(9):805-814.
Caira et al., "Crystalline Polymorphism of Organic Compounds," Topics in Current Chemistry,. 1998, 198(36):163-208.
Caroff et al., "Treatment of tardive dyskinesia with tetrabenazine or valbenazine: a systematic review," J. Com. Eff. Research, 2017, 7(2):135-148.
Chinese Office Action in Chinese Application No. 201580023821.X, dated Jun. 20, 2018, 10 pages.
Citrome, "Valbenazine for tardive dyskinesia: A systematic review of the efficacy and safety profile for this newly approved novel medication—What is the number needed to treat, number needed to harm and likelihood to be helped or harmed?," Int J Clin Pract., 2017, e12964.
Cohen-Mansfield et al., "A description of agitation in a nursing home," J Gerontol., May 1989, 44(3):M77-M84.
Correll and Schenk, "Tardive dyskinesia and new antipsychotics," Curr Opin Psychiatry, Mar. 2008, 21(2):151-156.
Corvin, "Two patients walk into a clinic . . . A genomics perspective on the future of schizophreniam,". BMC Biol., 2011, 8 pages.
Cummings et al., "Deuterium tetrabenazine for tardive dyskinesia," Clinical Schizophrenia & Related Psychoses, 2018, 214-220.
Cummings et al., "The Neuropsychiatric Inventory: comprehensive assessment of psychopathology in dementia," Neurology, 1994, 44:2308-2314.
Davis et al., "Center for Drug Evaluation and Research," Medical Reviews(s), Jun. 1, 2017, Accessed on Sep. 30, 2020, retrieved from URL<https://www.accessdata.fda.gov/drugsatfda_docs/nda/2017/209241Origls000MedR.pdf>, 297 pages.
Derangula et al, "Liquid chromatography-tandem mass spectrometric assay for the determination of. tetrabenazine and its active metabolites in human plasma: a pharmacokinetic study," Biomedical Chromatography, Jun. 2013, 27(6):792-801.
Drug Development and Drug Interactions: Table of Substrates, Inhibitor and Inducers at https://www.fda.gov/drugs/developmentapprovalprocess/developmentesources/druginteractionslabeling/ucm093664.htm, U.S. Food and Drug Administration, 2017, 18 pages.
Erickson et al., "Reserpine- and tetrabenazine-sensitive transport of (3)H-histamine by the neuronal isoform of the vesicular monoamine transporter," Journal of Molecular Neuroscience, 1995, 6(4):277-287.
Eurasian Office Action in Eurasian Application No. 201890108, dated Oct. 30, 2018, 5 pages.
European Office Action in European Application No. 15734438.5, dated Jul. 17, 2018, 4 pages.
Extended European Search Report in European Appln. No. 16734150.2, dated Apr. 11, 2019, 7 pages.
Fahr, "Kapseln," Pharmazeutische Technologie, Jan. 2000, p. 237 (with machine English translation).
Fda.gov [online], U.S. Food & Drug Administration Drug Approvals and Databases, "Ingrezza (valbenazine) Capsules," dated Jun. 1, 2017, retrieved on Sep. 30, 2020, retrieved from URL<https://www.accessdata.fda.gov/drugsatfda_docs/nda/2017/209241OriglsOOOTOC.cfm>, 2 pages.
Fields et al., "Pill Properties that Cause Dysphagia and Treatment Failure," Current Therapeutic Research, Aug. 2015, 77:79-82.
Foster et al., "Deuterium isotope effects in the metabolism of drugs and xenobiotics: implications for drug design," Adv Drug Res., 1985, 14:1-36.
Gantois et al., "Restoring the phenotype of fragile X syndrome: insight from the mouse model," Curr Mol Med., Sep. 2001, 1(4):447-455.
Gately et al., "Deuterioglucose: alteration of biodistribution by an isotope effect," J Nucl Ned., 1986, 27(3):388-394.
Gordon et al., "The metabolism of the abortifacient terpene, (R)-(+)-pulegone, to a proximate toxin, menthofuran," Drug Metab Disp., 1987, 15(5):589-594.
Gottlieb et al., "NMR Chemical Shifts of Common Laboratory Solvents as Trace Impurities," J. Org. Chem. 1997, 62 (21): 7512-7515.
Grigoriadis et al., "Pharmacologic characterization of valbenazine (NBI-98854) and its metabolites," Journal of Pharmacology and Experimental Therapeutics, 2017, 361(3):454-461.
Guilloteau et al., "PET and SPECT exploration of central monoaminergic transporters for the development of new drugs and treatments in brain disorders," Current Pharmaceutical Design, Jan. 1, 2005, 11(25):3237-3245.
Gulieva et al., "Neuropharmacology analysis of the effect of olanzapine and clozapine on behavior characteristics and neuromodulator content in rat brain structure," Psychopharmacology and biological necrology, 2004, 585-589.
Guridi et al., "Clinical Features, Pathophysiology, and Treatment of Levodopa-Induced Dyskinesias in Parkinson's Disease," Parkinson's Disease, 2012, 1-15.
Harriot et al., "Identification of the First Selective Small Molecule BB2 Antagonists," Poster, Presented at the 249th ACS National Meeting & Exposition, Denver CO, Mar. 22-26, 2015, 1 page.
Hauser et al., "KINECT 3: A phase 3 randomized, double-blind, placebo-controlled trial of valbenazine for tardive dyskinesia," American Journal of Psychiatry, 2016, 174(5):476-484.
Healy et al., "Clozapine-reserpine combination for refractory psychosis," Schizophrenia Research, Jan. 1, 1997, 25:259-260.
Herrmann et al., "A Placebo-Controlled Trial of Valproate for Agitation and Aggression in Alzheimer's Disease," Dement Geriatr Cogn Disord., Jan. 2007, 23:116-119.
Hoare et al., "Conformational states of the corticotropin releasing factor 1 (CRF1) receptor: detection, and pharmacological evaluation by peptide ligands," Peptides, Dec. 2003,. 24(12):1881-1897.
Horev et al., "Dosage-dependent phenotypes in models of 16p11.2 lesions found in autism," Proc Natl Acad Sci USA., 2011, 108(41):17076-17081.
Howard et al., "Guidelines for the management of agitation in dementia," Int. J. Geriatr. Psychitry, Jul. 2001, 16(7):714-717.
Hu, "New Fluorescent Substrate Enables Quantitative and High-throughput Examination of Vesicular Monoamine Transporter 2 (VMAT2)," ACS Chem Biol. 2013, Sep. 20:8(9):1947-1954.
Ingrezza, Highlights of Prescribing Information, Neurocrine Biosciences, Inc., revised Oct. 2017, 15 pages.
Ingrezza, Patient Information, Neurocrine Biosciences, Inc., revised Oct. 2017, 1 page.
International Preliminary Report on Patentability in Appln. No. PCT/US2018/029255, dated Oct. 29, 2019, 7 pages.
International Preliminary Report on Patentability in International Application No. PCT/US2016/039098, dated Dec. 26, 2017, 8 pages.
International Preliminary Report on Patentability in International Application No. PCT/US2017/055877, dated Jul. 30, 2019, 11 pages.
International Preliminary Report on Patentability in International Application No. PCT/US2017/055931, dated Jul. 30, 2019, 16 pages.

(56) References Cited

OTHER PUBLICATIONS

International Preliminary Report on Patentability in International Application No. PCT/US2017/055965, dated Jul. 30, 2019, 8 pages.
International Preliminary Report on Patentability in International Application No. PCT/US2017/055980, dated Jul. 30, 2019, 7 pages.
International Preliminary Report on Patentability in International Appln. No. PCT/US2017/064196, dated Jun. 4, 2019, 6 pages.
International Report on Patentability in International Application No. PCT/US2015/029519, dated Nov. 8, 2016, 8 pages.
International Search Report and Written Opinion in Appln. No. PCT/US2017/055877, dated Dec. 26, 2019, 11 pages.
International Search Report and Written Opinion in Appln. No. PCT/US2017/055931, dated Dec. 11, 2017, 17 pages.
International Search Report and Written Opinion in Appln. No. PCT/US2017/55965, dated Dec. 5, 2017, 9 pages.
International Search Report and Written Opinion in Appln. No. PCT/US2018/029255, dated Jun. 26, 2018, 9 pages.
International Search Report and Written Opinion in Appln. No. PCT/US2017/55980, dated Dec. 1, 2017, 9 pages.
International Search Report and Written Opinion in International Application No. PCT/US2015/029519, dated Jun. 21, 2015, 11 pages.
International Search Report and Written Opinion in International Application No. PCT/US2016/039098, dated Nov. 22, 2016, 15 pages.
International Search Report and Written Opinion in International Appln. No. PCT/US2017/064196, dated Feb. 21, 2018, 10 pages.
International Search Report and Written Opinion in International Appln. No. PCT/US2019/46462, dated Nov. 7, 2019, 14 pages.
Jacq et al., "Development and validation of an automated static headspace gas chromatography-mass spectrometry (SHS-GC-MS) method for monitoring the formation of ethyl methane sulfonate from ethanol and methane sulfonic acid," J Pharm. Biomed Anal., 2008, 48(5):1339-1344.
Jankovic and Beach, "Long-term effects of tetrabenazine in hyperkinetic movement disorders," Neurology, Feb. 1, 1997, 48(2):359-362.
Jankovic et al., "Lesch-Nyhan Syndrome. A Study of Motor Behaviour and Cerebrospinal Fluid Neurotransmitters," Ann Neuro., May 1988, 23(5):466-469.
Jankovic., "Dopamine depleters in the treatment of hyperkinetic movement disorders," Expert Opinion on Pharmacotherapy, 17.18, 2016, 2461-2470.
Japanese Office Action in Japanese Application No. 2016-566238, dated Feb. 12, 2019, 13 pages.
Jiang, "Application of Deuteration in Drug Research,"Qilu Pharmacautical Affairs, Dec. 31, 2010, 29(11):682-684.
Jinnah et al., "Amphetamine-induced behavioral phenotype in a hypoxanthine-guanine phosphoribosyltransferase-deficient mouse model of Lesch-Nyhan syndrome," Behav Neurosci., Dec. 1991, 105(4):1004-1012.
Josiassen et al., "Long-term safety and tolerability of valbenazine (NBI-98854) in subjects with tardive dyskinesia and a diagnosis of Schizophrenia or mood disorder," Psychopharmacology Bulletin, 2017, 47(3):61-68.
Jul et al., "Hyperactivity with Agitative-Like Behavior in a Mouse Tauopathy Model," J Alzheimer's Dis., 2015, 49(3):783-795.
Katz et al., "Preclinical research in Rett syndrome: setting the foundation for translational success," Disease Models & Mechanisms, 2012, 5:733-745.
Kay et al., "The Positive and Negative Syndrome Scale (PANSS) for Schizophrenia," Schizophrenia Bulletin, 1987, 13:262-276.
Kazdoba et al., "Modeling fragile X syndrome in the Fmr1 knockout mouse," Intractable Rare Dis Res., Nov. 2014, 3(4):118-133.
Kenney et al., "Long-Term Tolerability of Tetrabenazine in the Treatment of Hyperkinetic Movement Disorders," Movement Disorders, 2007, 22(2):193-197.
Kenney et al., "Tetrabenazine in the treatment of hyperkinetic movement disorders," Expert Review Neurotherapeutics, 2006, 6(1):7-17.
Khalsa et al., "Treatment-resistant OCD: Options beyond first-line medications," Curr. Psychiatry, 2011, 10(11):45-52.
Kilbourn et al., "Absolute configuration of (+)-alpha-dihydrotetrabenazine, an active metabolite of tetrabenazine,"Chiralty, 1997, 9:(1)59-62.
Kilbourn et al., "Binding of alpha-dihydrotetrabenazine to the vesicular monoamine transporter is stereospecific," Eur J Pharmacol May 24 1995, 278(3):249-252.
Kilbourn et al., "In vivo binding of (+)-alpha-[3H]dihydrotetrabenazine to the vesicular monoamine transporter of rat brain: bolus vs. equilibrium studies," European Journal of Pharmacology, 1997, 331(2-3):161-168.
Kilbourn et al., "In vivo measures of dopaminergic radioligands in the rat brain: equilibrium vs. infusion studies," Synapse, Mar. 1 2002, 43(3):188-194.
Kim, "Valbenazine: First Global Approval," Drugs, 2017, 77:1123-1129.
Kimiagar er al., "Rapid improvement of tardive dyskinesia with tetrabenazine, clonazepam and clozapine combined: a naturalistic long-term follow-up study," J Neurol., Nov. 9, 2011, 259(4):660-664.
Koch et al., "Successful Therapy of Tardive Dyskinesia in a 71-year-old Woman with a combination of Tetrabenazine, Olanzapine and Tiapride," IJCP, Mar. 1, 2003, 57(2):147-149.
Kuehn et al., "A potential animal model for Lesch-Nyhan syndrome through introduction of HPRT mutations into mice," Nature, Mar. 1987, 326(6110):295-298.
Kurlan, "Treatment of Tourette Syndrome," Neurotherapeutics, 2014, 11:161-165.
Kushner et al., "Pharmacological uses and perspectives of heavy water and deuterated compounds," Can J Physiol Pharmacol., 1999, 77(2):79-88.
Lee et al., "In vitro and in vivo studies of benzisoquinoline ligands for the brain synaptic vesicle monoamine transporter," J. Med Chem., Jan. 5 1996, 39(1):191-196.
Lijinsky et al., "Dose-response studies in carcinogenesis by nitroso-N-methyl-N-(2-phenyl)ethylamine in rats and the effects of deuterium substitution," Food Cosmet. Toxicol., Aug. 1982, 20(4):393-399.
Lijinsky et al., "Dose-response studies with nitrosoheptamethyleneimine and its alpha-deuterium-labeled derivative in F344 rats," J Natl Cancer Inst., Nov. 1982, 69(5):1127-1133.
Loewen et al., "Evaluation of the potential for concomitant medications to affect valbenazine pharmacokinetics," Poster, Presented at the American Society of Clinical Psychopharmacology, May 29-Jun. 2, 2017. Miami, FL, 1 page.
Loewen et al., "Evaluation of the potential for valbenzaine to elicit drug interactions," Poster, Presented at the American Society of Clinical Psychopharmacology, May 29-Jun. 2, 2017: Miami, FL, 1 page.
Lombroso et al., "Tourette Syndrome and Obsessive-Compulsive Disorder ," Brain Dev., 2008, 30(4): 231-237.
Loriot et al., "Drug insight: gastrointestinal and hepatic adverse effects of molecular-targeted agents in cancer therapy," Nature Clinical Practice Oncology, 2008, 5(5):268-278.
Luo et al., "Single dose and repeat once-daily dose safety, tolerability, and pharmacokinetics of valbenazine in healthy male subjects," Poster, Presented at the American Psychiatric Association Annual Meeting, May 20-24, 2017, San Diego, CA, 1 page.
Madan, Invited Speaker, "NBI-98854. Human pharmacokinetics of NBI-98854 a selective inhibitory of VMAT2 with an attractive PK and safety profile for hyperkinetic movement disorders," Pipeline Projects Session, 12th annual meeting of American Society for Experimental NeuroTherapeutics, Bethesda, MD, 2010, 5 slides.
Madan, Invited Speaker, "NBI-98854: Selective inhibitor of VMAT2 with an attractive PK and safety profile for hyperkinetic movement disorders," Pipeline Projects Session, 11th annual meeting of American Society for Experimental NeuroTherapeutics, Arlington, VA, 2009, 9 slides.
Mangold et al., "Effects of deuterium labeling on azido amino acid mutagenicity in Salmonella typhimurium," Mutation Res., 1994, 308(1):33-42.

(56) References Cited

OTHER PUBLICATIONS

Marder et al., "Kinect 3: a randomized, double-blind, placebo-controlled phase 3 trial of valbenazine (NBI-98854) for Tardive Dyskinesia," American Academy of Neurology, 2016, 9 pages.
Margolese et al., "Tardive dyskinesia in the era of typical and atypical antipsychotics. Part 1: pathophysiology and mechanisms of induction," Can J Psychiatry, Aug. 2005, 50(9):541-47.
Material Safety Data Sheet. Product Name Valbenazine tosylate. Published May 1, 2014 (see Revision date). Retrieved from internet May 23, 2020. URL: https://www.selleckchem.com/msds/MSDS_S9500.pdf.
McBride et al., "Using Drosophila as a tool to identify Pharmacological Therapies for Fragile X Syndrome," Drug Discov Today Technol., Sep. 24, 2012, 10(1):e129-e136.
Mehvar et al., "Pharmacokinetics of tetrabenazine and its major metabolite in man and rat. Bioavailability and dose dependency studies," Drug Metabolism and Distribution, 1987, 15(2):250255.
mentalhealthamerica.net [online], "Depression," [retrieved on Dec. 17, 2018], retrieved from URL<http://www.mentalhealthamerica.net/conditions/depression>, 3 pages.
Mineur et al., "Social behavior deficits in the Fmr1 mutant mouse," Behav Breain Res., Mar. 15, 2006, 168(1):172-175.
Muller et al., "Valbenazine for the treatment of tardive dyskinesia," Expert Review of Neurotherapeutics, 2017, 17(2):1135-1144.
Muller, "Valbenazine granted breakthrough drug status for treating tardive dyskinesia," Expert Opin Investig Drugs, 2015, 24(6):737-42.
Near, "[3H]Dihydrotetrabenazine binding to bovine striatal synaptic vesicles," Mol. Pharmacol., Sep. 1986, 30:252-257.
Nikoloff et al., "Association between CYP2D6 genotype and tardive dyskinesia in Korean schizoprenics," The Pharmacogenomics J, 2002, 2:400-407.
ninds nih.gov [online], Available on or before Jan. 24, 2013, via Internet Archive: Wayback Machine URL <https://web.archive.org/web/20130124115120/www.ninds.nih.gov/disorders/rett/detail_rett.htm>, retrieved on Dec. 17, 2018], retrieved from URL<www ninds nih.gov/disorders/rett/detail_rett.htm>, 6 pages.
Nunes et al., "Effort-related motivational effects of the VMAT-2 inhibitor tetrabenazine: implications for animal models of the motivational symptoms of depression," J. Neurosci., 2013,. 33(49):19120-30.
Nyhan et al., "Lesch-Nyhan Syndrome," Posted Sep. 25, 2000[last update May 15, 2014], 21 pages.
O'Brien et al., "NBI-98854, a selective monoamine transport inhibitor for the treatment of tardive dyskinesia: a randomized, double-blind, placebo-controlled study," Movement Disorders, 2015, 30(12):1681-1687.
Ondo et al, "Tetrabenazine treatment for tardive dyskinesia: assessment by randomized videotape protocol," Am J Psychiatry, Aug. 1999, 156(8):1279-1281.
Owesson-White et al., "Sources contributing to the average extracellular concentration of dopamine in the nucleus accumbens," J Neurochem., 2012, 121:252-62.
Pallanti and Quercioli, "Treatment-refractory obsessive-compulsive disorder: methodological issues, operational definitions and therapeutic lines," Neuropsychopharmacol. Biol Psychiatry, May 2006, 30(3):400-412.
PCT International Preliminary Report on Patentability in International Appln. No. PCT/US2018/051579, dated Apr. 2, 2020, 25 pages.
PCT International Search Report and Written Opinion in International Appln. No. PCT/US2018/051579, dated Mar. 18, 2019, 36 pages.
Piccinni et al., "Effectiveness of a Clozapine-Aripiprazole Combination in Tourette Syndrome and Bipolar Spectrum Disorder," J Neuropsychiatry Clin Neurosci., Jan. 1, 2013, 25:1.
Pincus, "Management of digoxin toxicity," Aust. Prescr., 2016, 39(1):18-21.
Pittenger et al., "Pharmacological treatment of obsessive-compulsive disorder," Psychiatr. Clin. North Am., 2014, 37(3):375-391.
Poliak et al., "Juxtaparanodal clustering of Shaker-like K+ channels in myelinated axons depends on Caspr2 and TAG-1," J Cell Biol., Sep. 15, 2003, 162(6):1149-1160.
Porta et al., "Tourette's syndrome and role of tetrabenazine," Clin Drug Invest., 2008, 28(7):443-459.
Portman et al., "Behavioral abnormalities and circuit defects in the basal ganglia of a mouse model of 16p11.2 deletion syndrome," Cell Rep., May 22, 2014, 7(4):1077-1092.
Prescott, "Powder handling," Pharmaceutical Process Scale-Up, Jan. 2011, 195-209.
Preswick Pharmaceuticals et al., "Xenazine (tetrabenazine) tablets," 2008, retrieved from URL: https://accessdata.fda.gov/drugsatfda_docs/label/2011/021894s005lbl.pdj , retrieved on Jul. 28, 2020, 27 pages.
Provenzano et al., "Mutant mouse models of autism spectrum disorders," Dis. Markers, 2012, 33(5):225-239.
Rao et al, "Review article: metoclopramide and tardive dyskinesia," Aliment Pharmacol Ther 2010, 31(1):11-19.
Remington et al., "Tetrabenazine Augmentation in Treatment-Resistant Schizophrenia," Journal of Clinical Psychopharmacology, Feb. 1, 2012, 32(1):95-99.
Robey et al., "Modes and patterns of self-mutilation in persons with Lesch-Nyhan disease," Dev Med Child Neurol. Mar. 2003, 45(3):167-171.
Russian Office Action in Russian Application No. 2016147523, dated Dec. 27, 2018, 18 pages.
Sakimoto et al., "Phenotypic abnormalities in a chorea-acanthocytosis mouse model are modulated by strain background," Biochem Biophys Res Commun., 472(1):118-124 (2016).
Santus and Baker, "Osmotic drug delivery: a review of the patent literature," J. Controlled Release, 1995, 35(1)1-21.
Sawant, "Necessity of Establishing Chemical Integrity of Polymorphs of Drug Substance Using a Combination of NMR, HPLC, Elemental Analysis, and Solid-State Characterization Techniques: Case Studies," Organic Process Research & Development 17.3, 2013, :519-532.
Scherman et al., "[3H]dihydrotetrabenazine, a new in vitro monoaminergic probe for human brain," Journal of Neurochemistry 1988, 50(4):1131-1136.
Schneider et al., "Efficacy and adverse effects of atypical antipsychotics for dementia: meta-analysis of randomized, placebo-controlled trials," Am J Geritr Psychiatry., 2006, 14(3):191-210.
Schretlen et al., "Behavioral aspects of Lesch-Nyhan disease and its variants," Dev Med Child Neurol., Oct. 2005, 47(10):673-677.
Schretlen et al., "Neurocognitive functioning in Lesch-Nyhan disease and partial hypoxanthine-guanine phosphoribosyltransferase deficiency," J Int. Neuropsychol Soc., 2001, 7:805-812.
Scott et al., Making and Breaking Serotonin Neurons and Autism, Int J Devl Neuroscience., 2005, 23 :277-285.
Sever et al., "Process Analytical Technology in Solid Dosage Development and Manufacturing," Developing Solid Oral Dosage Forms Pharmaceutical Theory and Practice, Jan. 2008, 827-841.
Shen et al. "Safety and Efficacy of Tetrabenazine and use of Cocomitant Medications during Long-Term, Open-Label Treatment of Chorea Associated with Huntington's and Other Diseases," Tremor and Other Myperkinetic Movements, Oct. 22, 2013, https://tremorjournal.org/index.php/tremodarticle/view/191, pp. 1-12.
Siegert et al., "Efficacy and Safety of Valbenazine (NBI-98854) in Subjects with Tardive Dyskinesia: Results of a Long-Term Study (KINECT 3 Extension)," Poster Presented At the Xxii World Congress on Parkinson's Disease and Related Disorders, Nov. 12-15, 2017, 1 page.
Silverman et al., "Behavioural phenotyping assays for mouse models of autism," Nature Reviews Neuroscience, Jul. 2010, 11(7):490-502.
Simpson et al., "A rating scale for extrapyramidal side effects," Acta Psychiatry Scand Suppl, 1970, 212:11-19.
Singer et al., "Assessing the Effectiveness of Valbenazine in the Treatment of Tardive Dyskinesia as Determined by the AIMS and PGIC: Results from the KINECT 4 Trial," Poster Presented At the

(56) References Cited

OTHER PUBLICATIONS

22nd Annual International Congress of Parkinson's Disease and Movement Disorders, Oct. 5-9, 2018, 1 page.
Skor et al., "Differences in dihydrotetrabenazine isomer concentrations following administration of tetrabenazine and valbenazine," Drugs R D, 2017, 17:449-459.
Smolders et al., "Pharmacokinetics, efficacy, and safety of Hepatitis C virus drugs in patients with liver and/or renal impairment," Drug safety, 2016, 39(7):589-611.
Solon, "Risperidone-reserpine combination in refractory psychosis," Schizophrenia Research, Dec. 1, 1996, 22(3):265-266.
Spencer et al., "Social behavior in Fmrl knockout mice carrying a human FMR1 transgene," Behave. Neurosci., Jun. 2008, 122(3):710-715.
Spina et al., "Effect of fluoxetine on the plasma concentrations of clozapine and its major metabolites in patients with schizophrenia," International Clinical Psychopharmacology, May 1, 1998, 13(3):141-145.
STN CAS RN: 1639208-54-0, entered STN Dec. 22, 2014, 1 page.
Sun et al., "Preparation and evaluation of tetrabenazine enantiomers and all eight stereoisomers of dihydrotetrabenazine as VMAT2 inhibitors," Eur. J. Med. Chem., 2011, 46(5):1841-1848.
Table 14.3.5.14.1, "Young Mania Rating Scale (YMRS) Total Score and Change from Baseline (CFB) Values by Visit and Treatment Group," Neurocrine Biosciences, Inc., Oct. 8, 2015, 6 pages.
Tandon et al., "World Psychiatric Association Pharmacopsychiatry Section Statement on Comparative Effectiveness of Antipsychotics in the Treatment of Schizophrenia," Schizophrenia Research, Mar. 1, 2008, 100(1-3):20-38.
Tarsy and Baldessarini, "Epidemiology of tardive dyskinesia: is risk declining with modern antipsychotics?" Movement Disorders, May 2006, 21(5):589-598.
Tauber et al., "Elevated Levels of the Vesicular Monoamine Transporter and a Novel Repetitive Behavior in the Drosophila Model of Fragile X Syndrome," PLOS ONE, Nov. 2, 2011, 6(11):e27100.
Teasdale et al., "Mechanism and Processing Parameters Affecting the Formation of Methyl Methanesulfonate from Methanol and Methanesulfonic Acid: an Illustrative Example for Sulfonate Ester Impurity Formation," Org Process Res. Dev., 2009, 15:13429-433.
Teasdale, "Sulfonate Esters -How Real is the Risk? Summary of Key Findings from PQRI Studies of the Reaction Between Sulfonic acids and Alcohols," Product Quality Research Institute, 2007, 42 pages.
Teasdale, "Sulphonate esters: a real or imagined risk? PQRI studies to determine actual risk," British Pharmaceutical Conference, Manchester Sep. 10-12, 2007, J Pharmacy Pharmacol. A-78, Abstract 218.
Tenback et al, "Incidence and persistence of tardive dyskinesia and extrapyramidal symptoms in schizophrenia," J Psychopharmacol, Jul. 2010, 24(7):1031-1035.
Teng et al., "Lobeline displaces [3H]dihydrotetrabenazine binding and releases [3H]dopamine from rat striatal synaptic vesicles: comparison with d-amphetamine," J Neurochem. 1998, 71(1):258-265.
Thai-Curato et al., "Cardiovascular profile of valbenazine: analysis of pooled dated from three randomized, double-blind, placebo-controlled trials," Drug Safety, 2017, 41(4):429-440.
Tian et al., "CYP3A4-mediated pharmacokinetic interactions in cancer therapy," Curr. Drug Metab., 2014, 15(8):808-17.
Tomemori et al., "A gene-targeted mouse model for chorea-acanthocytosis," J Neurochem, 2005, 92(4):759-766.
Traynor, "Valbenazine approved for treatment of tardive dyskinesia," ASHP, Apr. 17, 2017, retrieved from URL: https://www.ashp.orginews/2017/04/17/valbenazine-approved-for-treatment-of-tardive-dyskinesia?loginreturnUrl=SSOCheckOnly, retrieved on Jun. 22, 2020, 3 pages.
Tsoussis et al., "Disclosure of cancer diagnosis: the Greek experience," JBUON, Open Access Journal aimed at the rapid diffusion of scientific knowledge in Oncology, 2013, 18(2):516-526.
United States Pharmacopoeia ("USP"), "Bulk Density and Tapped Density of Powders," <616>, 2015, 3 pages.
United States Pharmacopoeia ("USP"), "Disintegration," <701>, 2016, 4 pages.
United States Pharmacopoeia ("USP"), "Dissolution," <711>, 2011, 8 pages.
United States Pharmacopoeia ("USP"), "Uniformity of Dosage Units," <905>, 2016, 9 pages.
United States Pharmacopoeia, "Light Diffraction Measurement of Particle Size," <429>, 2016, 8 pages.
US Department of Health and Human Services, and Food and Drug Administration, "Size, Shape, and Other Physical Attributes of Generic Tablets and Capsules," Jun. 2015, 10 pages.
Verkerk et all., "Identification of a gene (FMR-1) containing a CGG repeat coincident with a breakpoint cluster region exhibiting length variation in fragile X syndrome," Cell, May 1991, 65(5):905-914.
Verma et al., "Formulation aspects in the development of osmotically controlled oral drug delivery systems," J. Controlled Release, Feb. 19 2002, 79(1-3):7-27.
Verma et al., "Osmotically controlled oral drug delivery," Drug Development and Industrial Pharmacy, Jul. 2000, 26(7):695-708.
Wade, "Deuterium isotope effects on noncovalent interactions between molecules," Chem Biol Interact., Feb. 1999, 117(3):191-217.
Watts et al., "Clinical and biochemical studioes on treatment of Lesch-Nylan Syndrome," Archives of Disease in Childhood., 1974, 49:693-702.
Weihe and Eiden, "Chemical neuroanatomy of the vesicular amine transporters.," The FASEB Journal, Dec. 2000, 14(15):2435-2449.
Woods et al, "Incidence of tardive dyskinesia with atypical versus conventional antipsychotic medications: a prospective cohort study," J Clin Psychiatry, Apr. 2010, 71(4):463-474.
Yamashita et al., "Modeling of rifampicin-induced CYP3A4 activation dynamics for the prediction of clinical drug-drug interactions in vitro data," PLoS One, 2013, 8(9):e70330, 11 pages.
Yasumoto et al "Inhibitory effect of selective serotonin reuptake inhibitors on the vesicular monoamine transporter 2," Neuroscience Letters, May 1, 2009, 454(3):229-232.
Zello et al., "Plasma and urine enrichments following infusion of L-[13C]phenylalanine and L- [ring-2H5]phenylalanine in humans evidence for an isotope effect in renal tubular reabsorption,". Metabolism, 1994, 43(4):487-491.
Zhang et al, "Synergistic Effects of Olanzapine and other Antipsychotic Agents in Combination with Fluoxetine on Norepinephrine and Dopamine release in rate Prefrontal Cortex," Neuropsychopharmacology, Sep. 1, 2000, 23(3):250-262.

\* cited by examiner

METHODS FOR THE ADMINISTRATION OF CERTAIN VMAT2 INHIBITORS

This application is a continuation of U.S. patent application Ser. No. 16/481,033, filed on Jul. 25, 2019, which is a 371 of International Application Number PCT/US2017/055877, filed on Oct. 10, 2017, which claims the benefit of U.S. Provisional Application No. 62/451,605, filed Jan. 27, 2017, which is incorporated herein by reference for all purposes.

Dysregulation of dopaminergic systems is integral to several central nervous system (CNS) disorders, including neurological and psychiatric diseases and disorders. These neurological and psychiatric diseases and disorders include hyperkinetic movement disorders, and conditions such as schizophrenia and mood disorders. The transporter protein vesicular monoamine transporter-2 (VMAT2) plays an important role in presynaptic dopamine release and regulates monoamine uptake from the cytoplasm to the synaptic vesicle for storage and release.

Despite the advances that have been made in this field, there remains a need for new therapeutic products useful to treatment of neurological and psychiatric diseases and disorders and other related diseases or conditions described herein. One such agent is valbenazine, which has the following chemical structure:

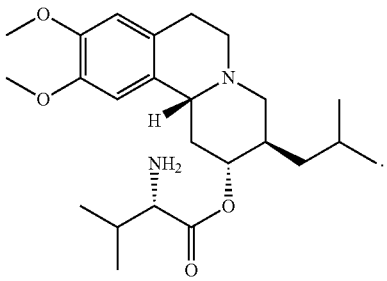 [SMILES: COc1cc2c(cc1OC)[C@H]1C[C@@H](OC(=O)[C@@H](N)C(C)C)[C@H](CC(C)C)CN1CC2]

A formulation of valbenazine:4-toluenesulfonate (1:2) (referred to herein as "valbenazine ditosylate") has been previously reported in the FDA approved drug label Ingrezza®.

The cytochrome P450 enzyme system (CYP450) is responsible for the biotransformation of drugs from active substances to inactive metabolites that can be excreted from the body. In addition, the metabolism of certain drugs by CYP450 can alter their PK profile and result in sub-therapeutic plasma levels of those drugs over time.

There are more than 1500 known P450 sequences which are grouped into families and subfamily. The cytochrome P450 gene superfamily is composed of at least 207 genes that have been named based on the evolutionary relationships of the cytochromes P450. For this nomenclature system, the sequences of all of the cytochrome P450 genes are compared, and those cytochromes P450 that share at least 40% identity are defined as a family (designated by CYP followed by a Roman or Arabic numeral, e.g., CYP3), and further divided into subfamilies (designated by a capital letter, e.g., CYP3A), which are comprised of those forms that are at least 55% related by their deduced amino acid sequences. Finally, the gene for each individual form of cytochrome P450 is assigned an Arabic number (e.g., CYP3A4).

CYP3A isoenzyme is a member of the cytochrome P450 superfamily which constitutes up to 60% of the total human liver microsomal cytochrome P450 and has been found in alimentary passage of stomach and intestines and livers. CYP3A has also been found in kidney epithelial cells, jejunal mucosa, and the lungs. CYP3A is one of the most abundant subfamilies in cytochrome P450 superfamily.

At least five (5) forms of CYPs are found in human CYP3A subfamily, and these forms are responsible for the metabolism of a large number of structurally diverse drugs. In non-induced individuals, CYP3A may constitute 15% of the P450 enzymes in the liver; in enterocytes, members of the CYP3A subfamily constitute greater than 70% of the CYP-containing enzymes.

CYP3A is responsible for metabolism of a large number of drugs including nifedipine, macrofide antibiotics including erythromycin and troleandomycin, cyclosporin, FK506, teffenadine, tamoxifen, lidocaine, midazolam, triazolam, dapsone, diltiazem, lovastatin, quinidine, ethylestradiol, testosterone, and alfentanil. CYP3A is involved in erythromycin N-demethylation, cyclosporine oxidation, nifedipine oxidation, midazolam hydroxylation, testosterone 6-β-hydroxylation, and cortisol 6-β-hydroxylation. CYP3A has also been shown to be involved in both bioactivation and detoxication pathways for several carcinogens in vitro.

There is a significant, unmet need for methods for administering a VMAT2 inhibitor, such as valbenazine or (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof, to a patient in need thereof, wherein the patient is also being treated with another substance which may interact with the VMAT2 inhibitor, such as a CYP3A4 inducer. The present disclosure fulfills these and other needs, as evident in reference to the following disclosure.

BRIEF SUMMARY

Provided is a method of administering a vesicular monoamine transport 2 (VMAT2) inhibitor chosen from valbenazine and (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof to a patient in need thereof, comprising: administering to the patient a therapeutically effective amount of the VMAT2 inhibitor and informing the patient or a medical care worker that co-administration of a strong cytochrome P450 3A4 (CYP3A4) inducer is not recommended.

Also provided is a method of administering a vesicular monoamine transport 2 (VMAT2) inhibitor chosen from valbenazine and (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof to a patient in need thereof wherein the patient is being treated with a strong cytochrome P450 3A4 (CYP3A4) inducer, comprising: discontinuing treatment of the strong CYP3A4 inducer and then administering the VMAT2 inhibitor to the patient, thereby avoiding the use of the VMAT2 inhibitor in combination with the strong CYP3A4 inducer.

These and other aspects of the invention will be apparent upon reference to the following detailed description. To this end, various references are set forth herein which describe in more detail certain background information, procedures, compounds, and/or compositions, and are each hereby incorporated by reference in their entirety.

DETAILED DESCRIPTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" or "a certain embodiment" means that a particular feature, structure or characteristic described in connection with the embodiment is included in at least one embodiment. Thus, the appearances of the phrases "in one embodiment" or "in an embodiment" or "in some embodiments" or "in a certain embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise.

As used herein, "valbenazine" may be referred to as (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester; or as L-Valine, (2R,3R,11bR)-1,3,4,6,7,11b-hexahydro-9,10-dimethoxy-3-(2-methylpropyl)-2H-benzo[a]quinolizin-2-yl ester or as NBI-98854.

As used herein, "(+)-α-HTBZ" means the compound which is an active metabolite of valbenazine having the structure:

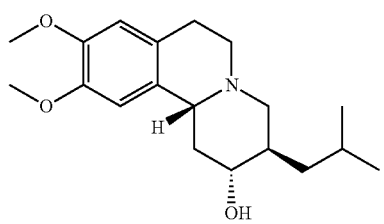 [SMILES: COc1cc2c(cc1OC)[C@H]1C[C@@H](O)[C@H](CC(C)C)CN1CC2]

(+)-α-HTBZ may be referred to as (2R, 3R, 11bR) or as (+)-α-DHTBZ or as (+)-α-HTBZ or as R,R,R-DHTBZ or as (+)-α-3-isobutyl-9,10-dimethoxy-1,3,4,6,7,11b-hexahydro-2H-pyrido[2,1-a]isoquinolin-2-ol; or as (2R, 3R,11bR)-3-isobutyl-9,10-dimethoxy-1,3,4,6,7,11b-hexahydro-2H-pyrido[2,1-a]isoquinolin-2-ol or as NBI-98782.

As used herein, "NBI-136110" means the compound which is a metabolite of valbenazine having the structure:

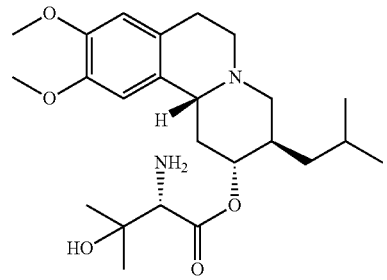 [SMILES: COc1cc2c(cc1OC)[C@H]1C[C@@H](OC(=O)[C@@H](N)C(C)(C)O)[C@H](CC(C)C)CN1CC2]

As used herein, "isotopic variant" means a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^{1}H$), deuterium ($^{2}H$), tritium ($^{3}H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^{1}H$), deuterium ($^{2}H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), and oxygen-18 ($^{18}O$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^{3}H$), carbon-11 ($^{11}C$), carbon-14 ($^{14}C$), nitrogen-13 ($^{13}N$), oxygen-14 ($^{14}O$), and oxygen-15 ($^{15}O$). It will be understood that, in a compound as provided herein, any hydrogen can be $^{2}H$, as example, or any carbon can be $^{13}C$, as example, or any nitrogen can be $^{15}N$, as example, and any oxygen can be $^{18}O$, as example, where feasible according to the judgment of one of skill in the art. In certain embodiments, an "isotopic variant" of a compound contains an unnatural proportion of deuterium.

With regard to the compounds provided herein, when a particular atomic position is designated as having deuterium or "D" or "d", it is understood that the abundance of deuterium at that position is substantially greater than the natural abundance of deuterium, which is about 0.015%. A position designated as having deuterium typically has a minimum isotopic enrichment factor of, in certain embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position. The isotopic enrichment of the compounds provided herein can be determined using conventional analytical methods known to one of ordinary skill in the art, including mass spectrometry, nuclear magnetic resonance spectroscopy, and crystallography.

As used herein, a substance is a "substrate" of enzyme activity when it can be chemically transformed by action of the enzyme on the substance. Substrates can be either activated or deactivated by the enzyme.

"Enzyme activity" refers broadly to the specific activity of the enzyme (i.e., the rate at which the enzyme transforms a substrate per mg or mole of enzyme) as well as the metabolic effect of such transformations.

A substance is an "inhibitor" of enzyme activity when the specific activity or the metabolic effect of the specific activity of the enzyme can be decreased by the presence of the substance, without reference to the precise mechanism of such decrease. For example, a substance can be an inhibitor of enzyme activity by competitive, non-competitive, allosteric or other type of enzyme inhibition, by decreasing expression of the enzyme, or other direct or indirect mechanisms. Co-administration of a given drug with an inhibitor may decrease the rate of metabolism of that drug through the metabolic pathway listed.

A substance is an "inducer" of enzyme activity when the specific activity or the metabolic effect of the specific activity of the enzyme can be increased by the presence of the substance, without reference to the precise mechanism of such increase. For example, a substance can be an inducer of enzyme activity by increasing reaction rate, by increasing expression of the enzyme, by allosteric activation or other direct or indirect mechanisms. Co-administration of a given drug with an enzyme inducer may increase the rate of excretion of the drug metabolized through the pathway indicated.

Any of these effects on enzyme activity can occur at a given concentration of active agent in a single sample, donor, or patient without regard to clinical significance. It is possible for a substance to be a substrate, inhibitor, or inducer of an enzyme activity. For example, the substance can be an inhibitor of enzyme activity by one mechanism and an inducer of enzyme activity by another mechanism. The function (substrate, inhibitor, or inducer) of the substance with respect to activity of an enzyme can depend on environmental conditions.

Lists of inhibitors, inducers and substrates for CYP3A4 can be found, for instance, at http://www.genemedrx.com/Cytochrome_P450_Metabolism_Table.php, and other sites and http://www.ildcare.eu/downloads/artseninfo/drugs_metabolized_by_cyp450s.pdf.

As used herein, a "strong CYP3A4 inducer" is a compound that decreases the area under the concentration time curve (AUC) of a sensitive index substrate of the CYP3A4 pathway by ≥80%. Index substrates predictably exhibit exposure increase due to inhibition or induction of a given metabolic pathway and are commonly used in prospective clinical drug-drug interaction studies. Sensitive index substrates are index substrates that demonstrate an increase in AUC of ≥5-fold with strong index inhibitors of a given metabolic pathway in clinical drug-drug interaction studies. Examples of sensitive index substrates for the CYP3A pathway are midazolam and triazolam. See, e.g., Drug Development and Drug Interactions: Table of Substrates, Inhibitor and Inducers at https://www.fda.gov/drugs/developmentapprovalprocess/developmentresources/druginteractionslabeling/ucm093664.htm.

As used herein, "hyperkinetic disorder" or "hyperkinetic movement disorder" or "hyperkinesias" refers to disorders or diseases characterized by excessive, abnormal, involuntary movements. These neurological disorders include tremor, dystonia, myoclonus, athetosis, Huntington's disease, tardive dyskinesia, Tourette syndrome, dystonia, hemiballismus, chorea, senile chorea, or tics.

As used herein, "tardive syndrome" encompasses but is not limited to tardive dyskinesia, tardive dystonia, tardive akathisia, tardive tics, myoclonus, tremor and withdrawal-emergent syndrome. Tardive dyskinesia is characterized by rapid, repetitive, stereotypic, involuntary movements of the face, limbs, or trunk.

As used herein, "about" means ±20% of the stated value, and includes more specifically values of ±10%, ±5%, ±2% and ±1% of the stated value.

As used herein, "AUC" refers to the area under the curve, or the integral, of the plasma concentration of an active pharmaceutical ingredient or metabolite over time following a dosing event.

As used herein "$AUC_{0-t}$" is the integral under the plasma concentration curve from time 0 (dosing) to time "t".

As used herein, "$AUC_{0-\infty}$" is the AUC from time 0 (dosing) to time infinity. Unless otherwise stated, AUC refers to $AUC_{0-\infty}$. Often a drug is packaged in a salt form, for example valbenazine ditosylate, and the dosage form strength refers to the mass of this salt form or the equivalent mass of the corresponding free base, valbenazine.

As used herein, "$C_{max}$" is a pharmacokinetic parameter denoting the maximum observed blood plasma concentration following delivery of an active pharmaceutical ingredient. $C_{max}$ occurs at the time of maximum plasma concentration, $t_{max}$.

As used herein, "co-administer" and "co-administration" and variants thereof mean the administration of at least two drugs to a patient either subsequently, simultaneously, or consequently proximate in time to one another (e.g., within the same day, or week or period of 30 days, or sufficiently proximate that each of the at least two drugs can be simultaneously detected in the blood plasma). When co-administered, two or more active agents can be co-formulated as part of the same composition or administered as separate formulations. This also may be referred to herein as "concomitant" administration or variants thereof.

As used herein, "adjusting administration", "altering administration", "adjusting dosing", or "altering dosing" are all equivalent and mean tapering off, reducing or increasing the dose of the substance, ceasing to administer the substance to the patient, or substituting a different active agent for the substance.

As used herein, "administering to a patient" refers to the process of introducing a composition or dosage form into the patient via an art-recognized means of introduction.

As used herein the term "disorder" is intended to be generally synonymous, and is used interchangeably with, the terms "disease," "syndrome," and "condition" (as in medical condition), in that all reflect an abnormal condition of the human or animal body or of one of its parts that impairs normal functioning, is typically manifested by distinguishing signs and symptoms.

As used herein, a "dose" means the measured quantity of an active agent to be taken at one time by a patient. In certain embodiments, wherein the active agent is not valbenazine free base, the quantity is the molar equivalent to the corresponding amount of valbenazine free base. For example, often a drug is packaged in a pharmaceutically acceptable salt form, for example valbenazine ditosylate, and the dosage for strength refers to the mass of the molar equivalent of the corresponding free base, valbenazine. As an example, 73 mg of valbenazine tosylate is the molar equivalent of 40 mg of valbenazine free base.

As used herein, "dosing regimen" means the dose of an active agent taken at a first time by a patient and the interval (time or symptomatic) at which any subsequent doses of the active agent are taken by the patient such as from about 20 to about 160 mg once daily, e.g., about 20, about 40, about 60, about 80, about 100, about 120, or about 160 mg once daily. The additional doses of the active agent can be different from the dose taken at the first time.

As used herein, "effective amount" and "therapeutically effective amount" of an agent, compound, drug, composition or combination is an amount which is nontoxic and effective for producing some desired therapeutic effect upon administration to a subject or patient (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "informing" means referring to or providing published material, for example, providing an active agent with published material to a user; or presenting information orally, for example, by presentation at a seminar, conference, or other educational presentation, by conversation between a pharmaceutical sales representative and a medical care worker, or by conversation between a medical care worker and a patient; or demonstrating the intended information to a user for the purpose of comprehension.

As used herein, "labeling" means all labels or other means of written, printed, graphic, electronic, verbal, or demonstrative communication that is upon a pharmaceutical product or a dosage form or accompanying such pharmaceutical product or dosage form.

As used herein, "a "medical care worker" means a worker in the health care field who may need or utilize information regarding an active agent, including a dosage form thereof, including information on safety, efficacy, dosing, administration, or pharmacokinetics. Examples of medical care workers include physicians, pharmacists, physician's assistants, nurses, aides, caretakers (which can include family members or guardians), emergency medical workers, and veterinarians.

As used herein, "Medication Guide" means an FDA-approved patient labeling for a pharmaceutical product conforming to the specifications set forth in 21 CFR 208 and other applicable regulations which contains information for patients on how to safely use a pharmaceutical product. A medication guide is scientifically accurate and is based on, and does not conflict with, the approved professional labeling for the pharmaceutical product under 21 CFR 201.57, but the language need not be identical to the sections of approved labeling to which it corresponds. A medication guide is typically available for a pharmaceutical product with special risk management information.

As used herein, "patient" or "individual" or "subject" means a mammal, including a human, for whom or which therapy is desired, and generally refers to the recipient of the therapy.

As used herein, "patient package insert" means information for patients on how to safely use a pharmaceutical product that is part of the FDA-approved labeling. It is an extension of the professional labeling for a pharmaceutical product that may be distributed to a patient when the product is dispensed which provides consumer-oriented information about the product in lay language, for example it may describe benefits, risks, how to recognize risks, dosage, or administration.

As used herein, "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, a "product" or "pharmaceutical product" means a dosage form of an active agent plus published material, and optionally packaging.

As used herein, "product insert" means the professional labeling (prescribing information) for a pharmaceutical product, a patient package insert for the pharmaceutical product, or a medication guide for the pharmaceutical product.

As used herein, "professional labeling" or "prescribing information" means the official description of a pharmaceutical product approved by a regulatory agency (e.g., FDA or EMEA) regulating marketing of the pharmaceutical product, which includes a summary of the essential scientific information needed for the safe and effective use of the drug, such as, for example indication and usage; dosage and administration; who should take it; adverse events (side effects); instructions for use in special populations (pregnant women, children, geriatric, etc.); safety information for the patient, and the like.

As used herein, "published material" means a medium providing information, including printed, audio, visual, or electronic medium, for example a flyer, an advertisement, a product insert, printed labeling, an internet web site, an internet web page, an internet pop-up window, a radio or television broadcast, a compact disk, a DVD, an audio recording, or other recording or electronic medium.

As used herein, "risk" means the probability or chance of adverse reaction, injury, or other undesirable outcome arising from a medical treatment. An "acceptable risk" means a measure of the risk of harm, injury, or disease arising from a medical treatment that will be tolerated by an individual or group. Whether a risk is "acceptable" will depend upon the advantages that the individual or group perceives to be obtainable in return for taking the risk, whether they accept whatever scientific and other advice is offered about the magnitude of the risk, and numerous other factors, both political and social. An "acceptable risk" of an adverse reaction means that an individual or a group in society is willing to take or be subjected to the risk that the adverse reaction might occur since the adverse reaction is one whose probability of occurrence is small, or whose consequences are so slight, or the benefits (perceived or real) of the active agent are so great. An "unacceptable risk" of an adverse reaction means that an individual or a group in society is unwilling to take or be subjected to the risk that the adverse reaction might occur upon weighing the probability of occurrence of the adverse reaction, the consequences of the adverse reaction, and the benefits (perceived or real) of the active agent. "At risk" means in a state or condition marked by a high level of risk or susceptibility. Risk assessment consists of identifying and characterizing the nature, frequency, and severity of the risks associated with the use of a product.

As used herein, "safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

As used herein, "$t_{max}$" is a pharmacokinetic parameter denoting the time to maximum blood plasma concentration following delivery of an active pharmaceutical ingredient As used herein, "$t_{1/2}$" or "plasma half-life" or "elimination half-life" or the like is a pharmacokinetic parameter denoting the apparent plasma terminal phase half-life, i.e., the time, after absorption and distribution of a drug is complete, for the plasma concentration to fall by half.

As used herein, "treating" or "treatment" refers to therapeutic applications to slow or stop progression of a disorder, prophylactic application to prevent development of a disorder, and/or reversal of a disorder. Reversal of a disorder differs from a therapeutic application which slows or stops a disorder in that with a method of reversing, not only is progression of a disorder completely stopped, cellular behavior is moved to some degree, toward a normal state that would be observed in the absence of the disorder.

As used herein, "VMAT2" refers to human vesicular monoamine transporter isoform 2, an integral membrane protein that acts to transport monoamines, particularly neurotransmitters such as dopamine, norepinephrine, serotonin, and histamine, from cellular cytosol into synaptic vesicles.

As used herein, the term "VMAT2 inhibitor", "inhibit VMAT2", or "inhibition of VMAT2" refers to the ability of a compound disclosed herein to alter the function of VMAT2. A VMAT2 inhibitor may block or reduce the activity of VMAT2 by forming a reversible or irreversible covalent bond between the inhibitor and VMAT2 or through formation of a noncovalently bound complex. Such inhibition may be manifest only in particular cell types or may be contingent on a particular biological event. The term "VMAT2 inhibitor", "inhibit VMAT2", or "inhibition of VMAT2" also refers to altering the function of VMAT2 by decreasing the probability that a complex forms between a VMAT2 and a natural substrate.

Provided is a method of administering a vesicular monoamine transport 2 (VMAT2) inhibitor chosen from val-benazine and (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof to a patient in need thereof, comprising: administering to the patient a therapeutically effective amount of the VMAT2 inhibitor and informing the patient or a medical care worker that co-administration of a strong cytochrome P450 3A4 (CYP3A4) inducer is not recommended.

In certain embodiments, the method further comprises determining whether the patient is being administered a strong CYP3A4 inducer.

In certain embodiments, the patient or medical care worker is informed that co-administration of the strong CYP3A4 inducer should be avoided or discontinued.

Also provided is a method of administering a vesicular monoamine transport 2 (VMAT2) inhibitor chosen from valbenazine and (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof to a patient in need thereof wherein the patient is being treated with a strong cytochrome P450 3A4 (CYP3A4) inducer, comprising: discontinuing treatment of the strong CYP3A4 inducer and then administering the VMAT2 inhibitor to the patient, thereby avoiding the use of the VMAT2 inhibitor in combination with the strong CYP3A4 inducer.

In certain embodiments, the strong CYP3A4 inducer is chosen from nevirapine, pentobarbital, phenytoin, lumacaftor, rifabutin, rifampicin, carbamazepine, fosphenytoin, phenobarbital, primidone, primidone, enzalutamide, mitotane, and St. John's Wort. In certain embodiments, the strong CYP3A4 inducer is chosen from rifampicin, carbamazepine, phenytoin, and St. John's Wort. In certain embodiments, the strong CYP3A4 inducer is rifampicin.

In certain embodiments, the VMAT2 inhibitor is administered to the patient to treat a neurological or psychiatric disease or disorder.

In certain embodiments, the neurological or psychiatric disease or disorder is a hyperkinetic movement disorder, mood disorder, bipolar disorder, schizophrenia, schizoaffective disorder, mania in mood disorder, depression in mood disorder, treatment-refractory obsessive compulsive disorder, neurological dysfunction associated with Lesch-Nyhan syndrome, agitation associated with Alzheimer's disease, Fragile X syndrome or Fragile X-associated tremor-ataxia syndrome, autism spectrum disorder, Rett syndrome, or chorea-acanthocytosis.

In certain embodiments, the neurological or psychiatric disease or disorder is a hyperkinetic movement disorder. In certain embodiments, the hyperkinetic movement disorder is tardive dyskinesia. In certain embodiments, the hyperkinetic movement disorder is Tourette's syndrome. In certain embodiments, the hyperkinetic movement disorder is Huntington's disease. In certain embodiments, the hyperkinetic movement disorder is tics. In certain embodiments, hyperkinetic movement disorder is chorea associated with Huntington's disease. In certain embodiments, the hyperkinetic movement disorder is ataxia, chorea, dystonia, Huntington's disease, myoclonus, restless leg syndrome, or tremors.

In certain embodiments, the VMAT2 inhibitor is administered orally.

In certain embodiments, the VMAT2 inhibitor is administered in the form of a tablet or capsule.

In certain embodiments, the VMAT2 inhibitor is administered with or without food.

In certain embodiments, the VMAT2 inhibitor is valbenazine or a pharmaceutically acceptable salt and/or isotopic variant thereof. In certain embodiments, the VMAT2 inhibitor is valbenazine or a pharmaceutically acceptable salt thereof. In certain embodiments, the VMAT2 inhibitor is a valbenazine tosylate salt. In certain embodiments, the VMAT2 inhibitor is a ditosylate salt of valbenazine. In certain embodiments, the VMAT2 inhibitor is an isotopic variant that is L-Valine, (2R,3R,11bR)-1,3,4,6,7,11b-hexahydro-9,10-di(methoxy-d$_3$)-3-(2-methylpropyl)-2H-benzo[a]quinolizin-2-yl ester or a pharmaceutically acceptable salt thereof.

In certain embodiments the VMAT2 inhibitor is (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof. In certain embodiments the VMAT2 inhibitor is (+)-α-3-isobutyl-9,10-dimethoxy-1,3,4,6,7,11b-hexahydro-2H-pyrido[2,1-a]isoquinolin-2-ol, or a pharmaceutically acceptable salt thereof. In certain embodiments the VMAT2 inhibitor is an isotopic variant that is (+)-α-3-isobutyl-9,10-di(methoxy-d$_3$)-1,3,4,6,7,11b-hexahydro-2H-pyrido[2,1-a]isoquinolin-2-ol or a pharmaceutically acceptable salt thereof.

In certain embodiments, the VMAT2 inhibitor is administered in an amount equivalent to between about 20 mg and about 160 mg of valbenazine free base. In certain embodiments, the VMAT2 inhibitor is administered in an amount equivalent to about 20 mg of valbenazine free base. In certain embodiments, the VMAT2 inhibitor is administered in an amount equivalent to about 40 mg of valbenazine free base. In certain embodiments, the VMAT2 inhibitor is administered in an amount equivalent to about 60 mg of valbenazine free base. In certain embodiments, the VMAT2 inhibitor is administered in an amount equivalent to about 80 mg of valbenazine free base. In certain embodiments, the VMAT2 inhibitor is administered in an amount equivalent to about 120 mg of valbenazine free base. In certain embodiments, the VMAT2 inhibitor is administered in an amount equivalent to about 160 mg of valbenazine free base.

In certain embodiments, the VMAT2 inhibitor is administered for a first period of time in a first amount and then the amount is increased to a second amount. In certain embodiments, the first period of time is a week. In certain embodiments, the first amount is equivalent to about 40 mg of valbenazine free base. In certain embodiments, the second amount is equivalent to about 80 mg of valbenazine free base.

In certain embodiments, the VMAT2 inhibitor is administered in an amount sufficient to achieve a maximal blood plasma concentration ($C_{max}$) of (+)-α-DHTBZ of between about 15 ng to about 60 ng per mL plasma and a minimal blood plasma concentration ($C_{min}$) of (+)-α-DHTBZ of at least 15 ng per mL plasma over an 8 hour period.

In certain embodiments, the VMAT2 inhibitor is administered in an amount sufficient to achieve a maximal blood plasma concentration ($C_{max}$) of (+)-α-DHTBZ of between about 15 ng to about 60 ng per mL plasma and a minimal blood plasma concentration ($C_{min}$) of approximately between about at least 33%-50% of the $C_{max}$ over a 12 hour period.

In certain embodiments, the VMAT2 inhibitor is administered in an amount sufficient to achieve: (i) a therapeutic concentration range of about 15 ng to about 60 ng of (+)-α-DHTBZ per mL plasma; and (ii) a threshold concentration of at least 15 ng (+)-α-DHTBZ per mL plasma over a period of about 8 hours to about 24 hours.

In certain embodiments, a method for treating neurological or psychiatric disease or disorders is provided herein that comprises administering to a subject a pharmaceutical composition comprising the VMAT2 inhibitor, in an amount sufficient to achieve a maximal blood plasma concentration ($C_{max}$) of R,R,R-DHTBZ of between about 15 ng to about 60 ng per mL plasma and a minimal blood plasma concentration ($C_{min}$) of R,R,R-DHTBZ of at least 15 ng per mL plasma over an 8 hour period.

In certain embodiments, the $C_{max}$ of R,R,R-DHTBZ is about 15 ng/mL, about 20 ng/mL, about 25 ng/mL, about 30 ng/mL, about 35 ng/mL, about 40 ng/mL, about 45 ng/mL, about 50 ng/mL, about 55 ng/mL or about 60 ng/mL plasma. In certain embodiments, the $C_{min}$ of R,R,R-DHTBZ is at least 15 ng/mL, at least 20 ng/mL, at least 25 ng/mL, at least 30 ng/mL, or at least 35 ng/mL plasma, over a period of 8 hrs, 12 hrs, 16 hrs, 20 hrs, 24 hrs, 28 hrs, or 32 hrs. In certain embodiments, the $C_{min}$ of R,R,R-DHTBZ is between about 15 ng/mL to about 35 ng/mL.

In certain embodiments, the pharmaceutical composition is administered in an amount sufficient to provide a $C_{max}$ of R,R,R-DHTBZ of about 15 ng/mL to about 60 ng/mL plasma and a $C_{min}$ of approximately at least 33% of the $C_{max}$ over a 24 hour period. In certain embodiments, the pharmaceutical composition is administered in an amount sufficient to provide a $C_{max}$ of R,R,R-DHTBZ of about 15 ng/mL to about 60 ng/mL plasma and a $C_{min}$ of approximately at least 50% of the $C_{max}$ over a 24 hour period. In certain embodiments, the pharmaceutical composition is administered in an amount sufficient to provide a $C_{max}$ of R,R,R-DHTBZ of about 15 ng/mL to about 60 ng/mL plasma and a $C_{min}$ of approximately between about at least 33%-50% of the $C_{max}$ over a 24 hour period.

In certain embodiments, the pharmaceutical composition is administered in an amount sufficient to provide a $C_{max}$ of R,R,R-DHTBZ of about 15 ng/mL to about 60 ng/mL plasma and a $C_{min}$ of approximately at least 33% of the $C_{max}$ over a 12 hour period. In certain embodiments, the pharmaceutical composition is administered in an amount sufficient to provide a $C_{max}$ of R,R,R-DHTBZ of about 15 ng/mL to about 60 ng/mL plasma and a $C_{min}$ of approximately at least 50% of the $C_{max}$ over a 12 hour period. In certain embodiments, the pharmaceutical composition is administered in an amount sufficient to provide a $C_{max}$ of R,R,R-DHTBZ of about 15 ng/mL to about 60 ng/mL plasma and a $C_{min}$ of approximately between about at least 33%-50% of the $C_{max}$ over a 12 hour period.

In certain embodiments, the pharmaceutical composition is administered to a subject in an amount that provides a $C_{max}$ of R,R,R-DHTBZ of about 15 ng/mL to about 60 ng/mL plasma and a $C_{min}$ of between about 5 ng/mL to about 30 ng/mL plasma over a 24 hour period. In certain embodiments, the pharmaceutical composition is administered to a subject in an amount that provides a $C_{max}$ of R,R,R-DHTBZ of about 15 ng/mL to about 60 ng/mL plasma and a $C_{min}$ of between about 7.5 ng/mL to about 30 ng/mL plasma over a 24 hour period.

In certain embodiments, a method for treating neurological or psychiatric disease or disorders is provided herein that comprises administering to a subject a pharmaceutical composition comprising the VMAT2 inhibitor, as an active pharmaceutical ingredient, in an amount sufficient to provide: (i) a therapeutic concentration range of about 15 ng to about 60 ng of R,R,R-DHTBZ per mL plasma; and (ii) a threshold concentration of at least 15 ng R,R,R-DHTBZ per mL plasma over a period of about 8 hours to about 24 hours.

In certain embodiments, the therapeutic concentration range is about 15 ng to about 35 ng, to about 40 ng, to about 45 ng, to about 50 ng, or to about 55 ng R,R,R-DHTBZ per mL plasma.

In certain embodiments, the threshold concentration of R,R,R-DHTBZ is about 15 ng/mL, about 20 ng/mL, about 25 ng/mL, about 30 ng/mL, about 35 ng/mL, about 40 ng/mL, about 45 ng/mL, about 50 ng/mL, about 55 ng/mL or about 60 ng/mL plasma, over a period of about 8 hrs, about 12 hrs, about 16 hrs, about 20 hrs, about 24 hrs, about 28 hrs, or about 32 hrs. In certain embodiments, the threshold concentration of R,R,R-DHTBZ is between about 15 ng/mL to about 35 ng/mL over a period of about 8 hours to about 24 hours.

Plasma concentrations may be measured by methods known in the art and generally by tandem mass spectroscopy.

Also provided is a vesicular monoamine transport 2 (VMAT2) inhibitor chosen from valbenazine and (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof, for use in a method of treating a neurological or psychiatric disease or disorder in a patient in need thereof wherein the patient has previously been determined to have discontinued treatment of a strong CYP3A4 inducer, comprising: administering to the patient a therapeutically effective amount of the VMAT2 inhibitor.

Also provided is a vesicular monoamine transport 2 (VMAT2) inhibitor chosen from valbenazine and (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof, for use in a method of treating a neurological or psychiatric disease or disorder in a patient in need thereof, comprising: determining if the patient is being administered a strong CYP3A4 inducer, selecting the patient for treatment where the patient is not being administered a strong CYP3A4 inducer, and administering to the selected patient a therapeutically effective amount of the VMAT2 inhibitor.

Also provided is a vesicular monoamine transport 2 (VMAT2) inhibitor chosen from valbenazine and (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof, for use in a method of treating a neurological or psychiatric disease or disorder in a patient in need thereof, comprising: administering to the patient a therapeutically effective amount of the VMAT2 inhibitor, subsequently determining whether the patient is being administered a strong CYP3A4 inducer, selecting the patient for treatment where the patient is not being administered a strong CYP3A4 inducer, and administering to the patient a therapeutically effective amount of the VMAT2 inhibitor.

Valbenazine can be prepared according to U.S. Pat. Nos. 8,039,627 and 8,357,697, the disclosure of each of which is incorporated herein by reference in its entirety. Tetrabenazine may be administered by a variety of methods including the formulations disclosed in PCT Publications WO 2010/018408, WO 2011/019956, and WO 2014/047167, the disclosure of each of which is incorporated herein by reference in its entirety. In certain embodiments, the valbenazine for use in the compositions and methods provided herein is in polymorphic Form I as disclosed in U.S. Pat. No. 10,065,952, the disclosure of which is incorporated herein by reference in its entirety.

Pharmaceutical Compositions

Also provided is a composition for treating a patient in need of a vesicular monoamine transport 2 (VMAT2) inhibitor chosen from valbenazine and (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof, comprising a therapeutically effective amount of the VMAT2 inhibitor, wherein the patient or a medical care worker is informed that co-administration of a strong cytochrome P450 3A4 (CYP3A4) inducer is not recommended.

In certain embodiments, the patient or medical care worker is informed that co-administration of the strong CYP3A4 inducer should be avoided or discontinued.

Also provided is a composition for treating a patient in need of a vesicular monoamine transport 2 (VMAT2) inhibitor chosen from valbenazine and (+)-α-3-isobutyl-9,10-dimethoxy-1,3,4,6,7,11b-hexahydro-2H-pyrido[2,1-a]isoquinolin-2-ol, or a pharmaceutically acceptable salt and/or isotopic variant thereof, and being treated with a strong cytochrome P450 3A4 (CYP3A4) inducer, comprising the VMAT2 inhibitor, wherein treatment of the strong CYP3A4 inducer is discontinued prior to administration of the composition to the patient, thereby avoiding the use of the composition in combination with the strong CYP3A4 inducer.

In certain embodiments, the composition is for treating a neurological or psychiatric disease or disorder.

In certain embodiments, the composition is administered in an amount equivalent to between about 20 mg and about 120 mg of valbenazine free base of the VMAT2 inhibitor. In certain embodiments, the composition is administered in an amount equivalent to about 20 mg of valbenazine free base of the VMAT2 inhibitor. In certain embodiments, the composition is administered in an amount equivalent to about 40 mg of valbenazine free base of the VMAT2 inhibitor. In certain embodiments, the composition is administered in an amount equivalent to about 80 mg of valbenazine free base of the VMAT2 inhibitor. In certain embodiments, the composition is administered in an amount equivalent to about 60 mg of valbenazine free base of the VMAT2 inhibitor. In certain embodiments, the composition is administered in an amount equivalent to about 120 mg of valbenazine free base of the VMAT2 inhibitor.

In certain embodiments, the composition is administered for a first period of time in a first amount of the VMAT2 inhibitor and then the amount is increased to a second amount. In certain embodiments, the first period of time is a week. In certain embodiments, the first amount is equivalent to about 40 mg of valbenazine free base. In certain embodiments, the second amount is equivalent to about 80 mg of valbenazine free base.

Also provided herein is a pharmaceutical composition for use in treating neurological or psychiatric disease or disorders, comprising the VMAT2 inhibitor as an active pharmaceutical ingredient, in combination with one or more pharmaceutically acceptable carriers or excipients.

The choice of excipient, to a large extent, depends on factors, such as the particular mode of administration, the effect of the excipient on the solubility and stability of the active ingredient, and the nature of the dosage form.

The pharmaceutical compositions provided herein may be provided in unit dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The pharmaceutical compositions provided herein may be administered alone, or in combination with one or more other compounds provided herein, one or more other active ingredients. The pharmaceutical compositions provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art). The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pregelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Vee gum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL®200 (W.R. Grace Co., Baltimore, Md.) and CAB-0-SIL® (Cabot Co. of Boston, Mass.); and mixtures thereof. The pharmaceutical compositions provided herein may contain about 0.1 to about 5% by weight of a lubricant. Suitable glidants include colloidal silicon dioxide, CAB-0-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation. The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems.

The pharmaceutical compositions provided herein may be provided as noneffervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide. Coloring and flavoring agents can be used in all of the above dosage forms. The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as antacids, proton pump inhibitors, and Hz-receptor antagonists.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

Parenteral Administration

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science.

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl phydroxybenzates, thimerosal, benzalkonium chloride, benzethonium chloride, methyl- and propylparabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including alpha-cyclodextrin, beta-cyclodextrin, hydroxypropyl-beta-cyclodextrin, sulfobutylether-beta-cyclodextrin, and sulfobutylether 7-beta-cyclodextrin (CAPTISOL®, CyDex, Lenexa, Kans.).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In certain embodiments, the pharmaceutical compositions are provided as ready-to-use sterile solutions. In certain embodiments, the pharmaceutical compositions are provided as sterile dry soluble products, including lyophilized powders and hypodermic tablets, to be reconstituted with a vehicle prior to use. In certain embodiments, the pharmaceutical compositions are provided as ready-to-use sterile suspensions. In certain embodiments, the pharmaceutical compositions are provided as sterile dry insoluble products to be reconstituted with a vehicle prior to use. In certain embodiments, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semisolid, or thixotropic liquid, for administration as an implanted depot. In certain embodiments, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, crosslinked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Topical Administration

The pharmaceutical compositions provided herein may be administered topically to the skin, orifices, or mucosa. The topical administration, as used herein, include (intra)dermal, conjuctival, intracorneal, intraocular, ophthalmic, auricular, transdermal, nasal, vaginal, uretheral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon bases, including such as lard, benzoinated lard, olive oil, cottonseed oil, and other oils, white petrolatum; emulsifiable or absorption bases, such as hydrophilic petrolatum, hydroxystearin sulfate, and anhydrous lanolin; water-removable bases, such as hydrophilic ointment; water-soluble ointment bases, including polyethylene glycols of varying molecular weight; emulsion bases, either water-in-oil (W/O) emulsions or oil-in-water (O/W) emulsions, including cetyl alcohol, glyceryl monostearate, lanolin, and stearic acid. These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinyl-alcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as 50 micrometers or less, or 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as /-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile- or pulsed-, controlled-, accelerated- and fast-, targeted-, programmed-release, and gastric retention dosage forms.

The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

The pharmaceutical compositions provided herein in a modified release dosage form may be fabricated using a matrix controlled release device known to those skilled in the art.

In certain embodiments, the pharmaceutical compositions provided herein in a modified release dosage form is formulated using an erodible matrix device, which is water swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acidglycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In certain embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as caranuba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients in the compositions.

The pharmaceutical compositions provided herein in a modified release dosage form may be prepared by methods known to those skilled in the art, including direct compression, dry or wet granulation followed by compression, melt-granulation followed by compression.

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-tolunesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water, as disclosed in U.S. Pat. No. 5,798,119. Such hydrophobic but water-permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes. The delivery port(s) on the semipermeable membrane may be formed postcoating by mechanical or laser drilling. Delivery port(s) may also be formed in situ by erosion of a plug of water-soluble material or by rupture of a thinner portion of the membrane over an indentation in the core. In addition, delivery ports may be formed during coating process.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients as described herein to promote performance or processing of the formulation.

The osmotic controlled-release dosage forms can be prepared according to conventional methods and techniques known to those skilled in the art.

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), hydroxylethyl cellulose, and other pharmaceutically acceptable excipients.

The pharmaceutical compositions provided herein in a modified release dosage form may be fabricated a multiparticulate controlled release device, which comprises a multiplicity of particles, granules, or pellets, ranging from about 10 pm to about 3 mm, about 50 pm to about 2.5 mm, or from about 100 pm to 1 mm in diameter. Such multiparticulates may be made by the processes know to those skilled in the art, including wet- and dry-granulation, extrusion/spheronization, roller-compaction, melt-congealing, and by spray-coating seed cores.

Other excipients as described herein may be blended with the pharmaceutical compositions to aid in processing and forming the multiparticulates. The resulting particles may themselves constitute the multiparticulate device or may be coated by various film forming materials, such as enteric polymers, water-swellable, and water-soluble polymers. The multiparticulates can be further processed as a capsule or a tablet.

Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems.

Dosages

In the treatment, prevention, or amelioration of one or more symptoms of tic disorders or other conditions, disorders or diseases associated with VMAT2 inhibition, an appropriate dosage level generally is about 0.001 to 100 mg per kg patient body weight per day (mg/kg per day), about 0.01 to about 80 mg/kg per day, about 0.1 to about 50 mg/kg per day, about 0.5 to about 25 mg/kg per day, or about 1 to about 20 mg/kg per day, which may be administered in single or multiple doses. Within this range the dosage may be 0.005 to 0.05, 0.05 to 0.5, or 0.5 to 5.0, 1 to 15, 1 to 20, or 1 to 50 mg/kg per day. In certain embodiments, the dosage level is about 0.001 to 100 mg/kg per day.

In certain embodiments, the dosage level is about from 25 to 100 mg/kg per day. In certain embodiments, the dosage level is about 0.01 to about 40 mg/kg per day. In certain embodiments, the dosage level is about 0.1 to about 80 mg/kg per day. In certain embodiments, the dosage level is about 0.1 to about 50 mg/kg per day. In certain embodiments, the dosage level is about 0.1 to about 40 mg/kg per day. In certain embodiments, the dosage level is about 0.5 to about 80 mg/kg per day. In certain embodiments, the dosage level is about 0.5 to about 40 mg/kg per day. In certain embodiments, the dosage level is about 0.5 to about 25 mg/kg per day. In certain embodiments, the dosage level is about 1 to about 80 mg/kg per day. In certain embodiments, the dosage level is about 1 to about 75 mg/kg per day. In certain embodiments, the dosage level is about 1 to about 50 mg/kg per day. In certain embodiments, the dosage level is about 1 to about 40 mg/kg per day. In certain embodiments, the dosage level is about 1 to about 25 mg/kg per day.

In certain embodiments, the dosage level is about from 5.0 to 150 mg per day, and in certain embodiments from 10 to 100 mg per day. In certain embodiments, the dosage level is about 80 mg per day. In certain embodiments, the dosage level is about 40 mg per day.

For oral administration, the pharmaceutical compositions can be provided in the form of tablets containing 1.0 to 1,000 mg of the active ingredient, particularly about 1, about 5, about 10, about 15, about 20, about 25, about 30, about 40, about 45, about 50, about 75, about 80, about 100, about 150, about 200, about 250, about 300, about 400, about 500, about 600, about 750, about 800, about 900, and about 1,000 mg of the active ingredient for the symptomatic adjustment of the dosage to the patient to be treated. In certain embodiments, the pharmaceutical compositions can be provided in the form of tablets containing about 100 mg of the active ingredient. In certain embodiments, the pharmaceutical compositions can be provided in the form of tablets containing about 80 mg of the active ingredient. In certain embodiments, the pharmaceutical compositions can be provided in the form of tablets containing about 75 mg of the active ingredient. In certain embodiments, the pharmaceutical compositions can be provided in the form of tablets containing about 50 mg of the active ingredient. In certain embodiments, the pharmaceutical compositions can be provided in the form of tablets containing about 40 mg of the active ingredient. In certain embodiments, the pharmaceutical compositions can be provided in the form of tablets containing about 25 mg of the active ingredient. The compositions may be administered on a regimen of 1 to 4 times per day, including once, twice, three times, and four times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds provided herein may also be combined or used in combination with other agents useful in the treatment, prevention, or amelioration of one or more symptoms of the diseases or conditions for which the compounds provided herein are useful, including tic disorders and other conditions commonly treated with antipsychotic medication.

In certain embodiments, the compounds provided herein may also be combined or used in combination with a typical antipsychotic drug. In certain embodiments, the typical antipsychotic drug is fluphenazine, haloperidol, loxapine, molindone, perphenazine, pimozide, sulpiride, thioridazine, or trifluoperazine. In certain embodiments, the antipsychotic drug is an atypical antipsychotic drug. In certain embodiments, the atypical antipsychotic drug is aripiprazole, asenapine, clozapine, iloperidone, olanzapine, paliperidone, quetiapine, risperidone, or ziprasidone. In certain embodiments, the atypical antipsychotic drug is clozapine.

Such other agents, or drugs, may be administered, by a route and in an amount commonly used thereof, simultaneously or sequentially with the compounds provided herein. When compounds provided herein are used contemporaneously with one or more other drugs, a pharmaceutical composition containing such other drugs in addition to the compounds provided herein may be utilized, but is not required. Accordingly, the pharmaceutical compositions provided herein include those that also contain one or more other active ingredients or therapeutic agents, in addition to the compounds provided herein.

The weight ratio of the compounds provided herein to the second active ingredient may be varied, and will depend upon the effective dose of each ingredient. Generally, an effective dose of each will be used. Thus, for example, when the compounds provided herein are used in combination with the second drug, or a pharmaceutical composition containing such other drug, the weight ratio of the particulates to the second drug may range from about 1,000:1 to about 1:1,000, or about 200:1 to about 1:200.

Combinations of the particulates provided herein and other active ingredients will generally also be within the aforementioned range, but in each case, an effective dose of each active ingredient should be used.

Examples of embodiments of the present disclosure are provided in the following examples. The following examples are presented only by way of illustration and to assist one of ordinary skill in using the disclosure. The examples are not intended in any way to otherwise limit the scope of the disclosure.

EXAMPLES

Example 1

A Phase 1, Open-Label, One-Sequence Crossover Study to Assess the Effect of Rifampin on the Pharmacokinetics of Valbenazine Tosylate in Healthy Subjects This was a Phase 1, open-label, one-sequence crossover, drug-interaction study of valbenazine tosylate in a total of 12 healthy subjects (6 males and 6 females). After providing informed consent, subjects were screened for eligibility to participate in the study within 21 days before Day 1 (the first day of study drug administration). Subjects who met the eligibility criteria were admitted to the study center on the morning of Day −1 (the day before dosing). Subjects received a single dose of 80 mg valbenazine tosylate on Days 1 and 11 between 0800 and 1000 hours. In addition, subjects received 600 mg rifampin (300 mg×2 capsules) once daily on Days 5 (after collection of the 96-hour PK sample) through 14 between 0830 and 1030 hours. Subjects were required to fast overnight before receiving the study drugs (valbenazine tosylate and rifampin). Subjects were discharged from the study center on Day 15 (final study day or upon early termination) after all safety evaluations and study assessments had been completed.

Blood samples were collected for PK analyses of NBI-98854 and its metabolites, NBI-98782 and NBI-136110, and for rifampin plasma concentrations at scheduled times during the study. Safety was assessed throughout the study.

NBI-98854 40 mg capsules were administered orally. The dose of NBI-98854 was based on ditosylate salt (dose expressed as free base). Subjects received a single dose of NBI-98854 80 mg (as two 40 mg capsules) twice during the study, on Days 1 and 11.

Rifampin 300 mg capsules were administered orally. Subjects received a single dose of rifampin 600 mg (as two 300 mg capsules) on Days 5 (after collection of the 96 hour NBI-98854 PK sample) through 14 between 0830 and 1030 hours.

Pharmacokinetics

Blood samples to determine plasma concentrations of NBI-98854, and the metabolites NBI-98782 and NBI-136110, were collected on Days 1 and 11 at 30 minutes before NBI-98854 dosing, and at 15, 30, and 45 minutes, and at 1, 1.5, 2, 3, 4, 8, 12, 18, 24, 48, 72, and 96 hours after NBI-98854 dosing or upon early termination.

The following plasma PK parameters were assessed for NBI-98854, NBI-98782, and NBI-136110:
  Area under the plasma concentration versus time curve (AUC) from 0 to 24 hours ($AUC_{0-24}$)
  AUC from 0 hours to last measureable concentration ($AUC_{tlast}$)
  AUC from 0 hours extrapolated to infinity ($AUC_{0-\infty}$)
  Maximum plasma concentration ($C_{max}$)
  Time prior to the first measurable concentration ($T_{lag}$)
  Apparent terminal half-life ($t_{1/2}$)
  Time to maximum plasma concentration ($t_{max}$)
  Apparent mean residence time (MRT)
  Molar ratio of the metabolites NBI-98782 and NBI-136110 to the parent drug NBI-98854

The following plasma PK parameters were calculated only for NBI-98854:
  Apparent systemic clearance after oral administration (CL/F)
  Apparent volume of distribution during the terminal phase after oral administration ($V_z/F$)

The PK data for $t_{max}$, $T_{lag}$, $t_{1/2}$, MRT, and Vz/F were rounded to 2 significant figures and all other parameters ($AUC_{0-24}$, $AUC_{tlast}$, $AUC_{0-\infty}$, $C_{max}$, and CL/F) were rounded to 3 significant figures. The last significant figure was rounded up if the digit to the right of it was >5, and was rounded down if the digit to the right of it was <4.

Blood samples to determine rifampin plasma concentration were collected at 30 minutes predose and 1, 2.5, 3.5, 7.5, 11.5, and 23.5 hours after rifampin dosing on Days 5 and 11; at 2.5 hours after rifampin dosing on Days 6 through 10 and Days 12 through 13; at 2.5 and 8 hours after rifampin dosing on Day 14; and at approximately 0800 hours on Day 15 (final study day or upon early termination). The following plasma PK parameters were calculated for rifampin: $AUC_{0-24}$, $AUC_{0-tlast}$, $C_{max}$, and $t_{max}$.

The PK data for $t_{max}$, $T_{lag}$, $t_{1/2}$, MRT, and Vz/F were rounded to 2 significant figures and all other parameters ($AUC_{0-24}$, $AUC_{0-tlast}$, $AUC_{0-\infty}$, $C_{max}$, and CL/F) were rounded to 3 significant figures. The last significant figure was rounded up if the digit to the right of it was ≥5, and was rounded down if the digit to the right of it was ≤4.

Pharmacokinetic Results

Concomitant administration of NBI-98854 and rifampin led to an approximate 30% decrease in $C_{max}$ and an approximate 70% decrease in $AUC_{0-\infty}$ of NBI-98854 compared with administration of NBI-98854 alone. The 90% confidence interval (CI) for the geometric mean ratios (57.9% to 80.3% for $C_{max}$ and 25.5% to 30.1% for $AUC_{0-\infty}$) were outside the 'no effect' range of 80% to 125% indicating an effect of treatment with rifampin on NBI-98854 $AUC_{0-\infty}$ and $C_{max}$. Mean $t_{1/2}$ of NBI-98854 decreased from 16 to 10 hours when NBI-98854 was administered with rifampin. This decrease in NBI-98854 $C_{max}$, $AUC_{0-\infty}$, and $t_{1/2}$ is consistent with in vitro data that suggests a significant role of rifampin-inducible cytochrome P450 (CYP) enzymes (eg, CYP3A4) in the metabolism of NBI-98854.

Coadministration of NBI-98854 and rifampin also led to an approximately 50% decrease in $C_{max}$ and an approximately 80% decrease in $AUC_{0-\infty}$ of an active metabolite NBI-98782 compared with administration of NBI-98854 alone. The 90% CI for the geometric mean ratios were outside the 'no effect' range of 80% to 125%. Mean $t_{1/2}$ of NBI-98782 decreased from 19 to 12 hours when NBI-98782 was administered with rifampin. This decrease in NBI-98782 $C_{max}$ and $AUC_{0-\infty}$ could be due to its decreased formation because of reduced bioavailability of NBI-98854 and/or increased metabolism of NBI-98782 by rifampin-inducible CYP enzymes (eg, CYP3A4).

For the metabolite NBI-136110, mean $C_{max}$ increased 1.4-fold; however, mean $AUC_{0-\infty}$ decreased approximately 70% after treatment with NBI-98854 plus rifampin compared with administration of NBI-98854 alone. The 90% CI for the geometric mean ratio was outside the 'no effect' range of 80% to 125%. Mean $t_{1/2}$ of NBI-136110 decreased from 27 to 12 hours when NBI-98854 was administered with rifampin. The increase in $C_{max}$ of NBI-136110 is consistent with the in vitro data, which suggests that CYP3A4 is involved in the conversion of NBI-98854 to NBI-136110. Additionally, the decrease in AUC and $t_{1/2}$ of NBI-136110 provides evidence that NBI-136110 is further metabolized by rifampin-inducible CYP enzymes (eg, CYP3A4).

| Summary of Pharmacokinetic Parameters | | |
|---|---|---|
| Parameter Statistic | NBI-98854 (80 mg) (N = 11) | NBI-98854 (80 mg) + Rifampin (600 mg) (N = 11) |
| $AUC_{0-24}$ (ng hr/mL) | | |
| Mean (SD) | 4480 (897) | 1510 (471) |
| Geometric CV % | 19.8 | 27.2 |
| $AUC_{0-tlast}$ (ng hr/mL) | | |
| Mean (SD) | 5930 (1180) | 1670 (555) |
| Geometric CV % | 20.0 | 27.8 |
| $AUC_{0-\infty}$ (ng hr/mL) | | |
| Mean (SD) | 6020 (1210) | 1700 (553) |
| Geometric CV % | 20.2 | 27.3 |
| $C_{max}$ (ng/mL) | | |
| Mean (SD) | 795 (386) | 542 (299) |
| Geometric CV % | 45.5 | 42.9 |
| $t_{max}$ (hours) | | |
| Median (mm, max) | 0.75 (0.50, 2.1) | 0.75 (0.50, 1.0) |
| $T_{last}$ (hours) | | |
| Mean (SD) | 0.12 (0.13) | 0.091 (0.13) |
| $t_{1/2}$ (hours) | | |
| Mean (SD) | 16 (2.3) | 10 (2.1) |
| Geometric CV % | 15 | 28 |
| MRT (hours) | | |
| Mean (SD) | 17 (2.8) | 8.7 (1.3) |
| Geometric CV % | 16 | 17 |
| CL/F (L/hr) | | |
| Mean (SD) | 13.8 (2.77) | 50.3 (11.4) |
| Geometric CV % | 20.2 | 27.3 |
| Vz/F (L) | | |
| Mean (SD) | 330 (79) | 730 (230) |
| Geometric CV % | 25 | 37 |

The geometric mean ratios and associated 90% CIs for $AUC_{0-\infty}$ and $C_{max}$ for NBI-98854 after treatment with NBI-98854 in combination with rifampin or NBI-98854 alone or are provided below.

| NBI-98854 Geometric Mean Ratios for Pharmacokinetic Exposure Parameters (PK Analysis Set) | | |
|---|---|---|
| Parameter | Ratio[a] (%) (NBI-98854 with rifampin vs. NBI-98854 alone) | 90% Confidence Interval[b] |
| $AUC_{0-\infty}$ (ng × hr/mL) | 27.7 | 25.5, 30.1 |
| $C_{max}$ (ng/mL) | 68.2 | 57.9, 80.3 |

[a]Ratio of geometric least-squares means was based on a mixed model using log-transformed (base 10) data
[b]The 90% confidence interval for geometric mean ratio was based on least-squares means using log-transformed (base 10) data Geometric mean ratios for $AUC_{0-\infty}$ and $C_{max}$ for NBI-98854 after administration of NBI-98854 in combination with rifampin compared with NBI-98854 alone were 27.7% and 68.2%, respectively. The corresponding upper and lower 90% CI bounds for $AUC_{0-\infty}$ (25.5% to 30.1%) and $C_{max}$ (57.9% to 80.3%) were outside the 'no effect' range of 80% to 125%, indicating an effect of treatment with rifampin on NBI-98854 $AUC_{0-\infty}$ and $C_{max}$.

PK parameters for NBI-98782 after treatment with NBI-98854 alone or in combination with rifampin are summarized below.

| Parameter Statistic | NBI-98854 (80 mg) (N = 11) | NBI-98854 (80 mg) + Rifampin (600 mg) (N = 11) |
|---|---|---|
| $AUC_{0-24}$ (ng × hr/mL) | | |
| Mean (SD) | 364 (90.9) | 115 (32.3) |
| Geometric CV % | 24.0 | 25.0 |
| $AUC_{0-tlast}$ (ng × hr/mL) | | |
| Mean (SD) | 665 (193) | 153 (43.9) |
| Geometric CV % | 26.0 | 23.7 |
| $AUC_{0-\infty}$ (ng × hr/mL) | | |
| Mean (SD) | 689 (203) | 156 (43.9) |
| Geometric CV % | 26.5 | 23.2 |
| $C_{max}$ (ng/mL) | | |
| Mean (SD) | 21.5 (4.60) | 11.2 (5.83) |
| Geometric CV % | 22.6 | 44.8 |
| $t_{max}$ (hr) | | |
| Median (min, max) | 4.0 (0.52, 18) | 3.0 (0.50, 4.0) |
| $T_{lag}$ (hr) | | |
| Mean (SD) | 0.25 (0.16) | 0.23 (0.075) |
| $t_{1/2}$ (hr) | | |
| Mean (SD) | 19 (2.3) | 12 (1.7) |
| Geometric CV % | 13 | 15 |
| MRT (hr) | | |
| Mean (SD) | 28 (3.8) | 17 (2.5) |
| Geometric CV % | 14 | 15 |

Mean $C_{max}$ for NBI-98782 after treatment with NBI-98854 plus rifampin was approximately 50% lower than that after treatment with NBI-98854 alone. Mean $AUC_{0-\infty}$ for NBI-98782 after treatment with NBI-98854 in combination with rifampin was approximately 80% lower than that after treatment with NBI-98854 alone. Median $t_{max}$ values were similar after treatment with NBI-98854 plus rifampin (3.0 hours) and NBI-98854 alone (4.0 hours) and mean $t_{1/2}$ was lower after treatment with NBI-98854 plus rifampin than after treatment with NBI-98854 alone (12 and 19 hours, respectively).

The variability in PK (ie, geometric CV %) for NBI-98782 after treatment with NBI-98854 alone and in combination with rifampin was generally similar for $AUC_{0-24}$, $AUC_{tlast}$, $t_{1/2}$, and MRT; but was higher for $C_{max}$ after NBI-98854 in combination with rifampin.

Geometric mean ratios for $AUC_{0-\infty}$ and $C_{max}$ for NBI-98782 after administration of NBI-98854 in combination with rifampin compared with NBI-98854 alone were 22.8% and 48.5%, respectively. The corresponding upper and lower 90% CI bounds for $AUC_{0-\infty}$ (20.5% to 25.4%) and $C_{max}$ (41.3% to 56.9%) were outside the 'no effect' range of 80% to 125%, indicating an effect of treatment with rifampin on NBI-98782 $AUC_{0-\infty}$ and $C_{max}$.

The mean NBI-136110 plasma concentration versus time profiles for NBI-98854 alone or in combination with rifampin are presented below.

| Parameter Statistic | NBI-98854 (80 mg) (N = 11) | NBI-98854 (80 mg) + Rifampin (600 mg) (N = 11) |
|---|---|---|
| $AUC_{0-24}$ (ng × hr/mL) | | |
| Mean (SD) | 963 (271) | 554 (133) |
| Geometric CV % | 39.8 | 22.3 |
| $AUC_{0-tlast}$ (ng × hr/mL) | | |
| Mean (SD) | 1890 (451) | 658 (166) |
| Geometric CV % | 28.3 | 22.4 |
| $AUC_{0-\infty}$ (ng × hr/mL) | | |
| Mean (SD) | 2080 (463) | 663 (166) |
| Geometric CV % | 24.0 | 22.3 |
| $C_{max}$ (ng/mL) | | |
| Mean (SD) | 59.8 (16.9) | 81.5 (24.6) |
| Geometric CV % | 45.7 | 29.6 |
| $t_{max}$ (hr) | | |
| Median (min, max) | 3.0 (2.0, 8.0) | 1.5 (0.75, 2.1) |
| $T_{lag}$ (hr) | | |
| Mean (SD) | 0.23 (0.14) | 0.16 (0.13) |
| $t_{1/2}$ (hr) | | |
| Mean (SD) | 27 (6.7) | 12 (3.0) |
| Geometric CV % | 21 | 23 |
| MRT (hr) | | |
| Mean (SD) | 39 (11) | 12 (1.5) |
| Geometric CV % | 23 | 13 |

Mean $C_{max}$ was approximately 1.4-fold higher after treatment with NBI-98854 in combination with rifampin than that after treatment with NBI-98854 alone. Mean $AUC_{0-\infty}$ for NBI-136110 after treatment with NBI-98854 in combination with rifampin was approximately 70% lower than that after treatment with NBI-98854 alone. Median $t_{max}$ was 1.5 hours shorter (1.5 hours versus 3.0 hours) after treatment with NBI-98854 in combination with rifampin than that after treatment with NBI-98854 alone. Mean $t_{1/2}$ for NBI-136110 after treatment with NBI-98854 in combination with rifampin was approximately 40% shorter than that after treatment with NBI-98854 alone. The variability in PK (ie, geometric CV %) for NBI-136110 after treatment with NBI-98854 alone and in combination with rifampin was generally similar for $AUC_{tlast}$ and $t_{1/2}$; but was lower for $AUC_{0-24}$, MRT, and $C_{max}$ after NBI-98854 in combination with rifampin.

Geometric mean ratios for $AUC_{0-\infty}$ and $C_{max}$ for NBI-136110 after administration of NBI-98854 in combination with rifampin compared with NBI-98854 alone were 31.9% and 139.5%, respectively. The 90% CI for $AUC_{0-\infty}$ (28.9% to 35.2%) and $C_{max}$ (112.3% to 173.3%) were outside the "no effect" range of 80% to 125%, indicating an effect of treatment with rifampin on NBI-136110 $AUC_{0-\infty}$ and $C_{max}$.

Concomitant administration of NBI-98854 and rifampin led to an approximate 30% decrease in $C_{max}$ and an approximate 70% decrease in $AUC_{0-\infty}$ of NBI-98854 compared with administration of NBI-98854 alone. The 90% CI for the geometric mean ratios (57.9% to 80.3% for $C_{max}$ and 25.5% to 30.1% for $AUC_{0-\infty}$ were outside the 'no effect' range of 80% to 125% indicating an effect of treatment with rifampin on NBI-98854 $AUC_{0-\infty}$ and $C_{max}$. Mean $t_{1/2}$ of NBI-98854 decreased from 16 to 10 hours when NBI-98854 was administered with rifampin. This decrease in NBI-98854 $C_{max}$ and AUC is consistent with in vitro data that suggests a significant role of rifampin-inducible CYP enzymes (eg, CYP3A4) in the metabolism of NBI-98854.

Concomitant administration of NBI-98854 and rifampin also led to an approximate 50% decrease in $C_{max}$ and an approximate 80% decrease in $AUC_{0-\infty}$ of an active metabolite NBI-98782 compared with administration of NBI-98854 alone. The 90% CI for the geometric mean ratios were outside the 'no effect' range of 80% to 125%. Mean $t_{1/2}$ of NBI-98782 decreased from 19 to 12 hours when NBI-98854 was administered with rifampin. This decrease in NBI-98782 $C_{max}$ and AUC could be due to its decreased formation because of reduced bioavailability of NBI-98854 and/or increased metabolism of NBI-98782 by rifampin-inducible CYP enzymes (eg, CYP3A4).

For the metabolite NBI-136110, mean $C_{max}$ increased 1.4-fold; however, mean $AUC_{0-\infty}$ decreased approximately 70% after treatment with NBI-98854 plus rifampin compared with administration of NBI-98854 alone. The 90% CI for the geometric mean ratio was outside the 'no effect' range of 80% to 125%. Mean $t_{1/2}$ of NBI-136110 decreased from 27 to 12 hours when NBI-98854 was administered with rifampin. The increase in $C_{max}$ of NBI-136110 is consistent with the in vitro data, which suggests that CYP3A4 is involved in the conversion of NBI-98854 to NBI-136110. Additionally, the decrease $AUC_{0-\infty}$ of NBI-136110 provides evidence that NBI-136110 is further metabolized by rifampin-inducible CYP enzymes (eg, CYP3A4).

Safety

Safety was assessed based on adverse events (AEs), clinical laboratory tests, vital signs, physical examinations, and electrocardiograms (ECGs).

Statistical Methods: Plasma concentrations of NBI-98854, its metabolites, NBI-98782 and NBI-136110, and rifampin were summarized with descriptive statistics and in figures. An analysis of variance (ANOVA) model was used to compare $AUC_{0-\infty}$ and $C_{max}$ for NBI-98854 administered with rifampin ("test") versus $AUC_{0-\infty}$ and $C_{max}$ for NBI-98854 alone ("reference"). The PK parameters for metabolites of NBI-98854 and rifampin were also evaluated. Safety data were summarized using descriptive statistics.

Safety Results

No deaths, serious or severe treatment-emergent adverse events (TEAEs), or discontinuations due to an AE were reported in this study. All 12 subjects (100%) experienced chromaturia after beginning rifampin. Chromaturia is a known side effect of rifampin. The other most frequently reported AE was headache (3 subjects, 25.0%).

There were no important differences in the number and types of AEs reported across treatments, with the exception of chromaturia. There were no clinically significant changes in clinical laboratory test results, vital sign measurements, or ECG parameters during the study and no clinically important differences were noted across groups. Most subjects had normal physical examinations during the study and none of the abnormal findings were considered clinically significant. There were no important changes in body weight from baseline to the final visit. No subject had a corrected QT interval using Fridericia's formula (QTcF) interval >450 msec or a maximum increase from baseline >30 msec.

The number and percentage of subjects who experienced TEAEs are summarized by treatment below.

Number and Percentage of Subjects Who Experienced a Treatment-Emergent Adverse Event (Safety Analysis Set)

| Preferred Term | NBI-98854 (80 mg)[a] N = 12 n (%) | Rifampin (600 mg)[b] N = 12 n (%) | NBI-98854 (80 mg) + Rifampin (600 mg)[c] N = 11 n (%) |
|---|---|---|---|
| Overall | 6 (50.0) | 12 (100) | 1 (9.1) |
| Abdominal pain | 1 (8.3) | 0 | 0 |
| Abdominal pain upper | 0 | 1 (8.3) | 1 (9.1) |
| Non-cardiac chest pain | 0 | 1 (8.3) | 0 |
| Vessel puncture site haemorrhage | 1 (8.3) | 0 | 0 |
| Arthropod bite | 1 (8.3) | 0 | 0 |
| Headache | 3 (25.0) | 0 | 1 (9.1) |
| Hypoaesthesia | 0 | 0 | 1 (9.1) |
| Paraesthesia | 0 | 1 (8.3) | 0 |
| Chromaturia | 0 | 12 (100) | 0 |

[a]Onset on or after the first dose (Day 1) of NBI-98854 but prior to the first dose of rifampin
[b]Onset on or after the first dose of rifampin but prior to the Day 11 dose of NBI-98854 plus rifampin
[c]Onset on or after the Day 11 dose of NBI-99854 plus rifampin
Note:
Subjects may have more than one TEAE per system organ class or preferred term.

Conclusions

The major metabolic clearance pathways for NBI-98854 are ester hydrolysis to form an active metabolite NBI-98782 and mono-oxidation to form NBI-136110. In vitro studies have indicated the hydrolysis of NBI-98854 to form NBI-98782 can occur both enzymatically (via esterases) and non-enzymatically (via chemical hydrolysis), whereas CYP3A4/5 is the major enzyme involved in the oxidative metabolism of NBI-98854. The oxidative metabolism of the metabolite NBI-98782 is mediated primarily by CYP2D6 with contribution from CYP3A4/5 (and possibly other enzymes). Given the role of CYP enzymes in the metabolism and elimination of NBI-98854, pleiotropic CYP inducer like rifampin would be expected to decrease the systemic exposure to NBI-98854 and its metabolites.

The data from the present study provided clinical data demonstrating that concomitant administration of NBI-98854 and rifampin results in decrease in systemic exposure to NBI-98854, which is consistent with a significant role of inducible CYP enzymes (eg, CYP3A4) in the metabolism of NBI-98854. Systemic exposure to NBI-98782 was decreased, which could be due to (1) reduced bioavailability of NBI-98854 and/or (2) increased metabolism of NBI-98782 by rifampin-inducible CYP enzymes (eg, CYP3A4). The effect of rifampin on NBI-136110 exposure measures was characterized by an increase in $C_{max}$, but a decrease in AUC. The increase in $C_{max}$ of NBI-136110 is consistent with the in vitro data which suggests that CYP3A4 is involved in the conversion of NBI-98854 to NBI-136110. Induction of this pathway would be expected to increase the rate of formation of NBI-136110, as evidenced by an increase in $C_{max}$. Conversely, the decrease in $AUC_{0-\infty}$ and $t_{1/2}$ of NBI-136110 provides evidence that NBI-136110 is metabolized and eliminated by hepatic CYP enzymes.

Overall, NBI-98854 was well tolerated in this study. No deaths or serious or severe TEAEs were reported and no subject discontinued the study due to a TEAE. There were no clinically significant changes in clinical laboratory test results, vital sign measurements, or ECG parameters during the study.

Concomitant administration of NBI-98854 and rifampin results in a decrease in systemic exposure to NBI-98854 and NBI-98782.

NBI-98854 80 mg was well tolerated in healthy subjects when administered alone or concomitantly with rifampin.

Example 2: Pharmacologic Characterization of Valbenazine, Tetrabenazine, and Metabolite Thereof Upon oral administration, TBZ is reduced to form four discrete isomeric secondary alcohol metabolites, collectively referred to as dihydrotetrabenazine (DHTBZ), which contains three asymmetric carbon centers (C-2, C-3, and C-11β), which could hypothetically result in eight stereoisomers. However, because the C-3 and C-11β carbons have fixed relative configurations, only four stereoisomers are possible: (R,R,R-DHTBZ or (+)-α-DHTBZ (alternate nomenclature) or NBI-98782 (laboratory nomenclature); S,S,S-DHTBZ or (−)-α-DHTBZ or NBI-98771; S,R,R-DHTBZ or (+)-β-DHTBZ or NBI-98795; and R,S,S-DHTBZ or (−)-β-DHTBZ or NBI-98772.

The affinity of each compound was measured by inhibition of [$^3$H]-DHTBZ binding to rat forebrain membranes. The affinities relative to R,R,R-DHTBZ were also calculated and are presented. Data are reported as both the negative logarithm of the Ki (pKi) for statistical calculation with the normally distributed binding parameter used to determine the mean and SEM. The Ki value was determined from the mean pKi as 10(−pKi). The R,R,R-DHTBZ stereoisomer binds with the highest affinity to both rat and human VMAT2 (Ki=1.0 to 4.2 nM). In comparison, the remaining three DHTBZ stereoisomers (S,R,R-DHTBZ, S,S,S-DHTBZ, R,S,S-DHTBZ) bind to VMAT2 with a Ki values of 9.7, 250, and 690 nM, respectively.

In Vitro VMAT2 Binding Affinity in Rat Forebrain

| | VMAT2 | | | |
| --- | --- | --- | --- | --- |
| Compound | $K_i$, nm | pK$_i$ mean (SEM) | N | Affinity Relative to R,R,R-DHTBZ[a] |
| R,R,R-DHTBZ | 4.2 | 8.38 (0.42) | 27 | 1.0 |
| S,R,R-DHTBZ | 9.7 | 8.01 (0.32) | 6 | 2.3 |
| S,S,S-DHTBZ | 250 | 6.60 (0.22) | 4 | 60 |
| R,S,S-DHTBZ | 690 | 6.16 (0.05) | 5 | 160 |

[a]Affinity relative to R,R,R-DHTBZ was calculated using the $K_i$ value determined in the same study The primary metabolic clearance pathways of valbenazine (VBZ, NBI-98854) are hydrolysis (to form R,R,R-DHTBZ) and mono-oxidation (to form the metabolite NBI-136110). R,R,R-DHTBZ and NBI-136110, the two most abundant circulating metabolites of VBZ, are formed gradually and their plasma concentrations decline with half-lives similar to VBZ.

VBZ and its metabolites, R,R,R-DHTBZ and NBI-136110, were tested for their ability to inhibit the binding of [3H]-DHTBZ to VMAT2 in cell lines or native tissues. The affinity of each compound was measured by inhibition of [$^3$H]-DHTBZ binding to either human platelets or rat striatal membranes. The affinities relative to R,R,R-DHTBZ were also calculated and are presented. Data are reported as both the negative logarithm of the $K_i$ (pKi) for statistical calculation with the normally distributed binding parameter used to determine the mean and SEM (n=4 for each compound in each tissue). The $K_i$ value was determined from the mean pKi as $10^{(-pKi)}$. The primary metabolite R,R,R-DHTBZ, was the most potent inhibitor of VMAT2 in rat striatum and human platelet homogenates.

In Vitro VMAT2 Binding Affinity of Valbenazine and its Metabolites

| | Rat Striatum | | | Human Platelets | | |
| --- | --- | --- | --- | --- | --- | --- |
| Compound | $K_i$, nm | pK$_i$ mean (SEM) | Affinity Relative to R,R,R-DHTBZ | $K_i$, nm | pK$_i$ mean (SEM) | Affinity Relative to R,R,R-DHTBZ |
| Valbenazine | 110 | 6.95 (0.02) | 39 | 150 | 6.82 (0.02) | 45 |
| R,R,R-DHTBZ | 1.98 | 8.70 (0.09) | 1.0 | 3.1 | 8.52 (0.03) | 1.0 |
| NBI-136610 | 160 | 6.80 (0.02) | 57 | 220 | 6.65 (0.04) | 67 |

VBZ and NBI-136110 had similar effects on VMAT2 inhibition, but with Ki values that were approximately 40-65 times the Ki values (lower affinity) of R,R,R-DHTBZ. These results were corroborated by the radioligand binding assay of DHTBZ stereoisomers (i.e., TBZ metabolites) in the rat forebrain, which also showed R,R,R-DHTBZ to be the most potent inhibitor of VMAT2, followed by S,R,R-DHTBZ. Comparatively, S,S,S-DHTBZ and R,S,S-DHTBZ, the other two primary metabolites of TBZ, were found to be poor VMAT2 inhibitors with affinities approximately 60 and 160 times weaker than R,R,R-DHTBZ.

The affinity of VBZ and its metabolites R,R,R-DHTBZ and NBI-136110 for other targets beyond VMAT2 was assessed in an extensive Cerep screen of multiple classes of protein targets including GPCRs, cell-surface monoamine transporters, and ion channels including the cardiac potassium channel, human ether-a-go-go-related gene (HERG).

The multi-target activity screen of more than 80 targets for these compounds (Cerep screen) demonstrated that VBZ and its metabolites, R,R,R-DHTBZ and NBI-136110, did not inhibit the binding of cognate ligands to any of the targets by more than 50% at concentrations of 1-10 µM. In contrast, the other three DHTBZ stereoisomers (S,R,R-DHTBZ, S,S,S-DHTBZ, R,S,S-DHTBZ), which are metabolites of TBZ but not VBZ, demonstrated >50% inhibition of ligand binding to a number of receptor subtypes including serotonin, dopamine and adrenergic receptors. Results expressed as percent of control specific binding: (tested compound specific binding/control specific binding)×100. All compounds were tested at 1 or 10 µM final concentration and results are an excerpt of a larger 80 target panel performed as an initial screen at Cerep (n=2 for each compound at each target). Bolded results (>50%) indicate activity at target receptor.

| In Vitro Activity Of Valbenazine And DHTBZ Stereoisomers At Dopamine, Serotonin, And Adrenergic Receptors | | | | |
|---|---|---|---|---|
| Receptor Target | Valbenazine | R,R,R-DHTBZ | S,R,R-DHTBZ | S,S,S-DHTBZ/ R,S,S-DHTBZ[a] |
| Serotonin5-HT$_{1A}$ | 26 | 17 | 69 | 96 |
| Serotonin5-HT$_{2A}$ | 1 | −4 | 3 | 84 |
| Serotonin5-HT$_7$ | 4 | 3 | 80 | 98 |
| Dopamine D$_1$ | 8 | −6 | −5 | 82 |
| Dopamine D$_{2(s)}$ | 2 | 6 | 25 | 89 |

[a]For purposes of the broad panel screen, the S,S,S- and R,S,S-metabolites were tested as a 50/50 mixture.

To describe the monoamine systems in greater detail, detailed radioligand binding assays were performed for dopamine, serotonin and adrenergic receptor subtypes as well as the transporters for dopamine (DAT), serotonin (SERT), and norepinephrine (NET) for the common metabolite of TBZ and VBZ (R,R,R-DHTBZ) and the other relevant metabolites unique to TBZ and VBZ. This detailed analysis revealed the high specificity of R,R,R-DHTBZ for the VMAT2 transporter and the non-specific activities of the other TBZ metabolites, including relatively high affinity for dopamine and serotonin receptor subtypes. Interestingly, the R,R,R-DHTBZ metabolite showed the greatest non-selectivity with respect to the monoamine receptors. None of the TBZ or VBZ metabolites had any affinity for the monoamine transporters DAT, SERT or NET. To complete the selectivity profile for VMAT2, the functional activity for the human VMAT1 transporter of these compounds was tested in cells expressing VMAT1. While the non-selective irreversible high-affinity uptake inhibitor of VMAT1, reserpine, substantially inhibited uptake through VMAT1, there was no significant inhibitory activity of TBZ, VBZ, or its metabolites R,R,R-DHTBZ or NBI-136110 at concentrations up to 10 μM. For both VMAT1 and VMAT2, uptake was measured in the untransfected host cells and was found to be similar to transfected cells in the presence of excess reserpine.

Radioligand binding assays and the broad panel screen indicate that in addition to varying potency at the VMAT2 transporter, two of the other DHTBZ metabolites of TBZ (S,S,S-DHTBZ and R,S,S-DHTBZ) interact with D1 and D2 receptors. Since VBZ is not metabolized to either of these DHTBZ stereoisomers, its effects on postsynaptic dopamine receptors either directly or indirectly through the metabolites are non-existent.

Moreover, results from the broad panel screen indicate that VBZ and its major metabolites (R,R,R-DHTBZ and NBI-136110) have little to no affinity for more than 80 binding sites, including receptors, monoamine transporters, and ion channels. This profile suggests a low potential for off-target pharmacological effects. In addition, uptake studies using TBZ, VBZ and its metabolites, R,R,R-DHTBZ and NBI-136110, confirmed the selectivity of these compounds for VMAT2 as they had no significant effect on the uptake of monoamines through VMAT1 compared to reserpine, a known VMAT1/VMAT2 inhibitor.

The selectivity and specificity of VBZ was distinctively demonstrated using two in vivo surrogate measures of pharmacological effects. Ptosis, known to occur via adrenergic activation and prolactin release from the pituitary, modulated through the D2 dopamine receptor, demonstrated the difference between treatment with TBZ and VBZ. TBZ, VBZ and R,R,R-DHTBZ induced ptosis in an equivalent manner. This confirms that the metabolites formed by dosing TBZ or VBZ, or dosing of the active metabolite itself (R,R,R-DHTBZ) all have activity at VMAT2 affecting presynaptic monoamine release, in this case, related to norepinephrine release specifically to induce ptosis. Following similar treatment, but this time using prolactin release as a surrogate for dopaminergic modulation, R,R,R-DHTBZ and VBZ (to a lesser extent) induced a similar increase in serum prolactin levels as TBZ.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of treating a patient with a hyperkinetic movement disorder, wherein the patient is being administered a strong cytochrome P450 3A4 (CYP3A4) inducer, comprising:
   discontinuing treatment of the strong CYP3A4 inducer, and then
   orally administering once daily to the patient a therapeutically effective amount of a vesicular monoamine transporter 2 (VMAT2) inhibitor chosen from (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester and a pharmaceutically acceptable salt thereof, thereby avoiding the concomitant use of the VMAT2 inhibitor with the strong CYP3A4 inducer.

2. The method of claim 1, wherein the strong CYP3A4 inducer is chosen from nevirapine, pentobarbital, phenytoin, lumacaftor, rifabutin, rifampicin, carbamazepine, fosphenytoin, phenobarbital, primidone, enzalutamide, mitotane, and St. John's Wort.

3. The method of claim 1, wherein the strong CYP3A4 inducer is chosen from rifampicin, carbamazepine, phenytoin, and St. John's Wort.

4. The method of claim 1, wherein the strong CYP3A4 inducer is rifampicin.

5. The method of claim 1, wherein the VMAT2 inhibitor is administered in the form of a capsule.

6. The method of claim 1, wherein the hyperkinetic movement disorder is tardive dyskinesia.

7. The method of claim 1, wherein the hyperkinetic movement disorder is chorea.

8. The method of claim 1, wherein the hyperkinetic movement disorder is chorea associated with Huntington's disease.

9. The method of claim 1, wherein the VMAT2 inhibitor is a pharmaceutically acceptable salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

10. The method of claim 1, wherein the VMAT2 inhibitor is a ditosylate salt of (S)-2-amino-3-methyl-butyric acid (2R,3R, 11bR)-3-isobutyl-9,10-dimethoxy-1,3,4,6,7,11b-hexahydro-2H-pyrido[2,1-a]isoquinolin-2-yl ester.

11. The method of claim 1, wherein the ditosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester is in polymorphic Form I.

12. The method of claim 1, wherein the therapeutically effective amount is an amount equivalent to about 40 mg as measured by (S)-2-amino-3-methyl-butyric acid (2R,3R, 11bR)-3-isobutyl-9,10-dimethoxy-1,3,4,6,7,11b-hexahydro-2H-pyrido[2,1-a]isoquinolin-2-yl ester free base once daily for one week, and an amount equivalent to about 80 mg as measured by (S)-2-amino-3-methyl-butyric acid (2R,3R, 11bR)-3-isobutyl-9,10-dimethoxy-1,3,4,6,7,11b-hexahydro-2H-pyrido[2,1-a]isoquinolin-2-yl ester free base once daily after one week.

13. The method of claim 1, wherein the therapeutically effective amount is an amount equivalent to about 40 mg as measured by (S)-2-amino-3-methyl-butyric acid (2R,3R, 11bR)-3-isobutyl-9,10-dimethoxy-1,3,4,6,7,11b-hexahydro-2H-pyrido[2,1-a]isoquinolin-2-yl ester free base once daily.

14. The method of claim 1, wherein the therapeutically effective amount is an amount equivalent to about 60 mg as measured by (S)-2-amino-3-methyl-butyric acid (2R,3R, 11bR)-3-isobutyl-9,10-dimethoxy-1,3,4,6,7,11b-hexahydro-2H-pyrido[2,1-a]isoquinolin-2-yl ester free base once daily.

15. The method of claim 1, wherein the therapeutically effective amount is an amount equivalent to about 80 mg as measured by (S)-2-amino-3-methyl-butyric acid (2R,3R, 11bR)-3-isobutyl-9,10-dimethoxy-1,3,4,6,7,11b-hexahydro-2H-pyrido[2,1-a]isoquinolin-2-yl ester free base once daily.

\* \* \* \* \*